(12) United States Patent
Lee et al.

(10) Patent No.: US 11,139,436 B2
(45) Date of Patent: Oct. 5, 2021

(54) ORGANIC COMPOUND, AND LIGHT-EMITTING DIODE AND LIGHT-EMITTING DEVICE INCLUDING THE SAME

(71) Applicant: LG Display Co., Ltd., Seoul (KR)

(72) Inventors: Na-Yeon Lee, Paju-si (KR); Seung-Jae Lee, Paju-si (KR); Jong-Kwan Bin, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 360 days.

(21) Appl. No.: 16/172,417

(22) Filed: Oct. 26, 2018

(65) Prior Publication Data

US 2019/0131548 A1 May 2, 2019

(30) Foreign Application Priority Data

Oct. 26, 2017 (KR) .......................... 10-2017-0140169

(51) Int. Cl.
| | | |
|---|---|---|
| *H01L 51/50* | (2006.01) | |
| *H01L 51/00* | (2006.01) | |
| *C07D 495/04* | (2006.01) | |

(52) U.S. Cl.
CPC ........ *H01L 51/0074* (2013.01); *C07D 495/04* (2013.01); *H01L 51/0039* (2013.01);
(Continued)

(58) Field of Classification Search
None
See application file for complete search history.

(56) References Cited

U.S. PATENT DOCUMENTS

| | | |
|---|---|---|
| 2008/0171228 A1 | 7/2008 | Chen et al. |
| 2011/0315967 A1 | 12/2011 | Schmidhalter et al. |

(Continued)

FOREIGN PATENT DOCUMENTS

| | | |
|---|---|---|
| JP | H8-15879 A | 1/1996 |
| JP | 6744376 B2 | 8/2020 |

(Continued)

OTHER PUBLICATIONS

Kobayashi et al., "An Isomeric Series of Thiophene-Fused Tetracyanoquinodimethanes. I.# Preparation and Physico-Chemical Properties," *Bull. Chem. Soc. Jpn.* 65(8): 2168-2171 (1992).

(Continued)

*Primary Examiner* — Gregory D Clark
(74) *Attorney, Agent, or Firm* — Seed IP Law Group LLP

(57) ABSTRACT

Compounds useful dopants for light emitting diodes and light emitting display devices are disclosed. The compounds have the following structure (Formula I):

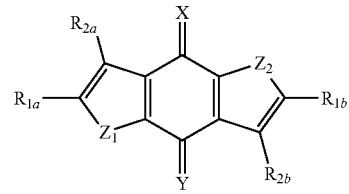

Formula 1 wherein $R_{1a}$, $R_{1b}$, $R_{2a}$, $R_{2b}$, $Z_1$, $Z_2$, X and Y are as defined herein. Light emitting diodes including the compounds of Formula I, light emitting devices including the same as well (Continued)

as methods associated with preparation and use of such compounds and devices are also provided.

18 Claims, 6 Drawing Sheets

(52) U.S. Cl.
CPC ........ *H01L 51/0043* (2013.01); *H01L 51/506* (2013.01); *H01L 51/5056* (2013.01)

(56) References Cited

U.S. PATENT DOCUMENTS

| | | | |
|---|---|---|---|
| 2017/0012237 A1* | 1/2017 | Sun | E21B 41/00 |
| 2017/0069850 A1* | 3/2017 | Hwang | H01L 51/0073 |
| 2019/1031548 | 5/2019 | Lee et al. | |

FOREIGN PATENT DOCUMENTS

| | | | | |
|---|---|---|---|---|
| KR | 10-2015-0027362 | * | 8/2013 | ............. H01L 51/50 |
| KR | 10-2015-0027362 A | | 3/2015 | |
| KR | 10-2017-0003472 A | | 1/2017 | |
| WO | 99/62909 A2 | | 12/1999 | |
| WO | 2011/161078 A1 | | 12/2011 | |
| WO | 2013/176325 A1 | | 11/2013 | |

OTHER PUBLICATIONS

Pomerantz et al., "Poly(benzo[1,2-b:4,5-b']dithiophene-4,8-diylvinylene). Synthesis, Properties, and Electronic Structure of a New Dithiophene-Fused p-Phenylenevinylene Conducting Polymer," *Macromolecules* 27(25):7478-7485 (1994).

* cited by examiner

ORGANIC COMPOUND, AND LIGHT-EMITTING DIODE AND LIGHT-EMITTING DEVICE INCLUDING THE SAME

CROSS-REFERENCE TO RELATED APPLICATIONS

This application claims the benefit under 35 U.S.C. § 119(a) of Korean Patent Application No. 10-2017-0140169, filed in Korea on Oct. 26, 2017, which is incorporated herein by reference in its entirety.

BACKGROUND

Technical Field

The present disclosure relates to an organic compound, and more particularly, to an organic compound with enhanced charge transfer properties, and a light-emitting diode and a light-emitting device each using the same and thus exhibiting enhanced luminous efficiency.

Description of the Related Art

Among flat panel display devices, organic light-emitting diode (OLED) display devices and quantum dot light-emitting diode (QLED) display devices can have a thin structure and have low power consumption, and thus are attracting attention as next-generation display devices that replace liquid crystal display (LCD) devices.

OLEDs or QLEDs are devices in which when charges are injected into an organic emissive layer disposed between an electron injection electrode (a cathode) and a hole injection electrode (an anode), electron-hole pairs are formed, and then disappear, whereby light is emitted. These OLEDs or QLEDs can be installed on a flexible transparent substrate such as a plastic substrate, can operate at a low voltage (10 V or less), have relatively low power consumption, and exhibit excellent color purity.

FIG. 1 is a schematic diagram illustrating bandgap energy levels of materials constituting electrodes and an emissive layer of a general OLED. Referring to FIG. 1, the OLED includes an anode and a cathode that face each other, an emitting material layer (EML) located between the anode and the cathode, a hole injection layer (HIL) and a hole transport layer (HTL) that are located between the anode and the EML, and an electron transport layer (ETL) located between the cathode and the EML.

As described above, OLEDs are devices in which when charge carriers are injected into an organic emissive layer disposed between an electron injection electrode (a cathode) and a hole injection electrode (an anode), electron-hole pairs are formed, and then disappear, whereby light is emitted. An EML is formed of an organic luminescent material, and holes and electrons respectively injected from an anode and a cathode recombine in the EML to form excitons. The organic luminescent material included in the EML is in an excited state by this energy, energy transition from the excited state to a ground state occurs in the organic luminescent material, and the generated energy is emitted as light.

Meanwhile, the HIL and the HTL inject and transport holes, which are positively charged carriers, from the anode to the EML, and the ETL injects and transports electrons, which are negatively charged carriers, from the cathode to the EML. In order for holes and electrons to be injected and transported into the EML, each layer should be formed of a material having an appropriate bandgap energy. Conventionally, an emissive layer constituting an OLED is formed through a deposition process, but recently, a solution process that may reduce waste of an organic material and does not require a color filter has been used to form an emissive layer.

For example, the HIL may be formed of poly(3,4-ethylenedioxythiophene) polystyrene sulfonate (PEDOT:PSS), the HTL may be formed of poly(4-butylphenyl-diphenyl-amine)(Poly-TPD), and the ETL may be formed of 2-biphenyl-4-yl-5-(4-t-butylphenyl)-1,3,4-oxadiazole (PBD).

However, a luminescent material constituting the EML has a very deep highest occupied molecular orbital (HOMO) energy level and a very high lowest unoccupied molecular orbital (LUMO) energy level. Thus, when holes are transported from the HTL to the EML and electrons are transported from the ETL to the EML, an energy barrier is formed due to a difference in energy level between the luminescent material of the EML and a material of a charge transfer layer adjacent thereto.

However, a difference ($\Delta G_H$) in HOMO energy level between the HTL and the EML is much greater than a difference ($\Delta G_L$) in LUMO energy level between the ETL and the EML. That is, the luminescent material of the EML has a much deeper HOMO energy level than that of an organic compound constituting the HTL. Thus, the transport and injection of holes into the EML are delayed more than the transport and injection of electrons into the EML, and accordingly, positively charged holes and negatively charged electrons cannot be injected in balance into the EML. In particular, in QLEDs which use, in the EML, an inorganic luminescent material having a much deeper HOMO energy level (a valence band energy level) than that of an organic material constituting the HTL, an imbalance between hole injection and electron injection more severely occurs.

When an excessive number of electrons is injected into the EML compared to holes, a considerable proportion of the excessive number of injected electrons disappears without recombining with holes and forming excitons. In addition, as electrons are more rapidly injected into the EML than holes, the electrons and the holes cannot be recombined in a luminescent material constituting the EML, but are recombined at an interface between the EML and the HTL. Accordingly, the luminous efficiency of a light-emitting diode is reduced, and a high driving voltage is required to generate a desired level of light emission, thus leading to an increase in power consumption.

Meanwhile, when thin films are formed through a solution process to manufacture a light-emitting diode having a structure in which a plurality of layers are stacked, a lower layer may be dissolved in a solvent used to form an upper layer, and mixing of materials may occur at an interface between the upper layer and the lower layer. That is, when neighboring emissive layers of a light-emitting diode manufactured through a solution process are stacked, a compatible solvent capable of dispersing and dissolving both a luminescent material of each of the neighboring emissive layers and/or a charge transporting material cannot be used.

Thus, in a light-emitting diode to which a solution process is to be applied, the type of solvent that can be used for each emissive layer is limited. Materials of the HTL which are capable of being dispersed and dissolved in a limitedly used solvent are also limited, and therefore, there is a need to develop a material capable of appropriately controlling a difference in energy level between an EML and an HTL.

BRIEF SUMMARY

Accordingly, the present invention is directed to an organic compound and a light emitting diode and a light emitting display device including the same that obviate one or more of the problems due to limitations and disadvantages of the related art.

An object of the present invention is to provide an organic compound, and a light-emitting diode and a light-emitting device in which balanced numbers of charges carriers, i.e., holes and electrons, may be injected into an emitting material layer due to an increased rate of a hole transfer into the emitting material layer.

Another object of the present invention is to provide an organic compound, and a light-emitting diode and a light-emitting device that exhibit enhanced luminous efficiency and can be operated at low voltage.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described herein, an organic compound is represented by following Formula 1:

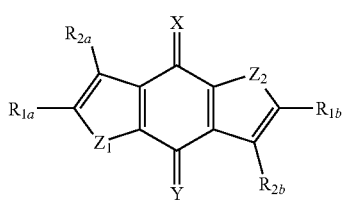

Formula 1 wherein each of $R_{1a}$, $R_{1b}$, $R_{2a}$ and $R_{2b}$ is independently hydrogen, deuterium, tritium, a halogen atom, a cyano group, a nitro group, an amine group, an unsubstituted or substituted $C_1$-$C_{20}$ aliphatic ester group, an unsubstituted or substituted $C_1$-$C_{20}$ alkyl amide group, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amine group, an unsubstituted or substituted $C_5$-$C_{30}$ aryl group, an unsubstituted or substituted $C_4$-$C_{30}$ heteroaryl group, an unsubstituted or substituted $C_5$-$C_{30}$ aralkyl group, an unsubstituted or substituted $C_4$-$C_{30}$ heteroaralkyl group, an unsubstituted or substituted $C_5$-$C_{30}$ aralkoxy group, an unsubstituted or substituted $C_4$-$C_{30}$ heteroaralkoxy group, an unsubstituted or substituted $C_5$-$C_{30}$ aryl amine group, or an unsubstituted or substituted $C_4$-$C_{30}$ heteroaryl amine group;

X is oxygen or $CR_5R_6$, wherein $R_5$ and $R_6$ are, at each occurrence, independently halogen, haloalkyl, cyano, nitro, $C_1$-$C_{20}$ alkyl, $C_5$-$C_{30}$ aryl, or $C_4$-$C_{30}$ heteroaryl, wherein each $C_1$-$C_{20}$ alkyl, $C_5$-$C_{30}$ aryl, and $C_4$-$C_{30}$ heteroaryl is optionally substituted with at least one substituent selected from the group consisting of cyano, nitro, and halogen;

Y is oxygen or $CR_7R_8$, wherein $R_7$ and $R_8$ are, at each occurrence, independently halogen, haloalkyl, cyano, nitro, $C_1$-$C_{20}$ alkyl, $C_5$-$C_{30}$ aryl, or $C_4$-$C_{30}$ heteroaryl, wherein each $C_1$-$C_{20}$ alkyl, $C_5$-$C_{30}$ aryl, and $C_4$-$C_{30}$ heteroaryl is optionally substituted with at least one substituent selected from the group consisting of cyano, nitro, and halogen, provided that X and Y are not the same; and $Z_1$ and $Z_2$ are each independently $NR_3$, S, or O, wherein $R_3$ is H or an unsubstituted or substituted $C_1$-$C_{20}$ alkyl group.

According to another aspect of another embodiment, an light emitting diode comprise first and second electrodes facing each other; and an emissive layer between the first and second electrodes and comprising a hole transfer layer of an organic material, wherein the hole transfer layer comprises the organic compound represented by Formula 1 above.

In an example embodiment, the organic compound may be used as a dopant of the hole transfer layer, and in this case, a triphenylamine-based organic material may be used as a host of the hole transfer layer.

According to an aspect of another embodiment, there is provided a light-emitting device (e.g., a light-emitting display device) including a substrate; the above-described light-emitting diode disposed on an upper portion of the substrate; and a driving device disposed between the substrate and the light-emitting diode and connected to the light-emitting diode.

Advantages and features of the disclosure will be set forth in part in the description, which follows and in part will become apparent to those having ordinary skill in the art upon examination of the following or may be learned from practice of the disclosure. Other advantages and features of the embodiments herein may be realized and attained by the structure particularly pointed out in the written description and claims hereof as well as the appended drawings.

It is to be understood that both the foregoing general description and the following detailed description are explanatory, and are intended to provide further explanation of the embodiments as claimed.

BRIEF DESCRIPTION OF THE SEVERAL VIEWS OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION

Figure 1:
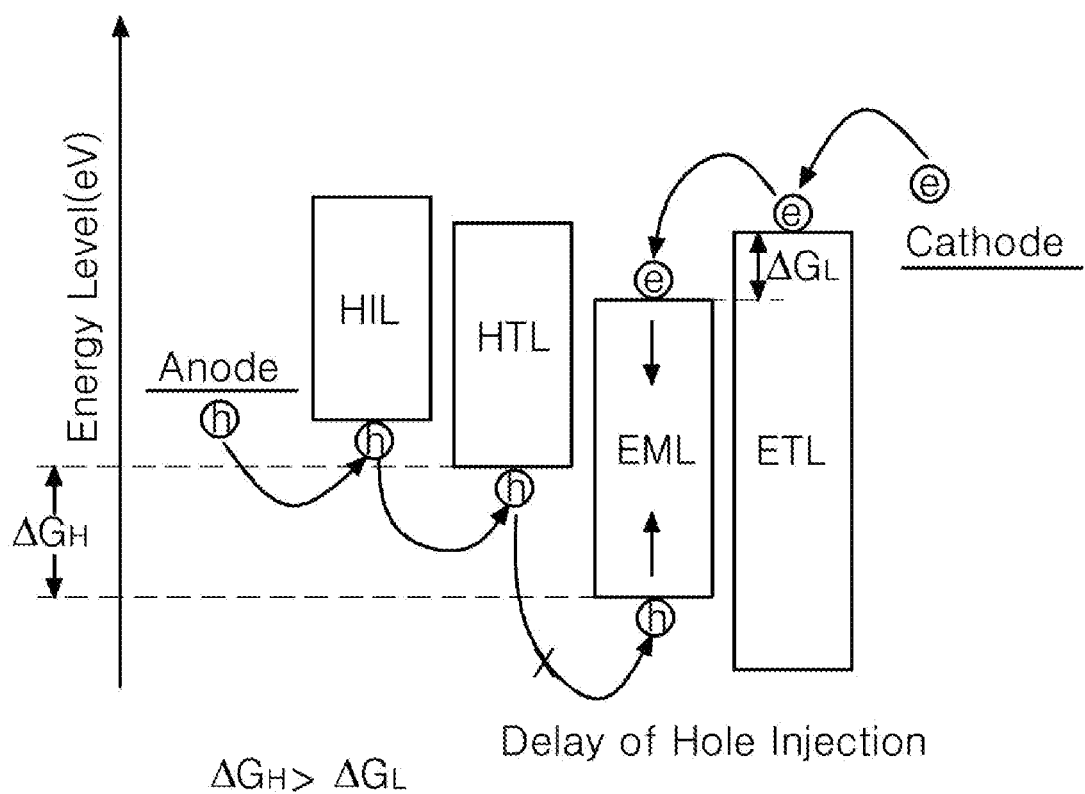
FIG. 1 is a schematic diagram illustrating energy levels of materials constituting electrodes and an emissive layer of an existing organic light-emitting diode.

Reference will now be made in detail to embodiments of the present disclosure, examples of which are illustrated in the accompanying drawings. In the following description, when a detailed description of well-known functions or configurations related to this document is determined to unnecessarily obscure the gist of an embodiment of the disclosure, the detailed description thereof will be omitted. The progression of processing steps and/or operations described is an example; however, the sequence of steps and/or operations is not limited to that set forth herein and may be changed as is known in the art, with the exception of steps and/or operations necessarily occurring in a certain order. Like reference numerals designate like elements throughout. Names of the respective elements used in the following explanations are selected only for convenience of writing the specification and thus may be different from those used in actual products.

Hereinafter, the present disclosure will be described with reference to the accompanying drawings as needed.

In a light-emitting diode, a compound used as a charge transporting material needs to have high charge mobility and inject balanced numbers of charge carriers into an emitting material layer. An organic compound according to an embodiment of the present disclosure may satisfy these properties and be represented by Formula 1 below:

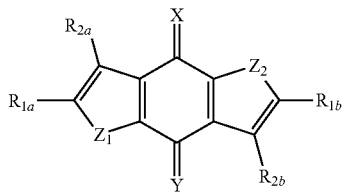

Formula 1 wherein each of $R_{1a}$, $R_{1b}$, $R_{2a}$ and $R_{2b}$ is independently hydrogen, deuterium, tritium, a halogen atom, a cyano group, a nitro group, an amine group, an unsubstituted or substituted $C_1$-$C_{20}$ aliphatic ester group, an unsubstituted or substituted $C_1$-$C_{20}$ alkyl amide group, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amine group, an unsubstituted or substituted $C_5$-$C_{30}$ aryl group, an unsubstituted or substituted $C_4$-$C_{30}$ heteroaryl group, an unsubstituted or substituted $C_5$-$C_{30}$ aralkyl group, an unsubstituted or substituted $C_4$-$C_{30}$ heteroaralkyl group, an unsubstituted or substituted $C_5$-$C_{30}$ aralkoxy group, an unsubstituted or substituted $C_4$-$C_{30}$ heteroaralkoxy group, an unsubstituted or substituted $C_5$-$C_{30}$ aryl amine group, or an unsubstituted or substituted $C_4$-$C_{30}$ heteroaryl amine group;

X is oxygen or $CR_5R_6$, wherein $R_5$ and $R_6$ are, at each occurrence, independently halogen, haloalkyl, cyano, nitro, $C_1$-$C_{20}$ alkyl, $C_5$-$C_{30}$ aryl, or $C_4$-$C_{30}$ heteroaryl, wherein each $C_1$-$C_{20}$ alkyl, $C_5$-$C_{30}$ aryl, and $C_4$-$C_{30}$ heteroaryl is optionally substituted with at least one substituent selected from the group consisting of cyano, nitro, and halogen;

Y is oxygen or $CR_7R_8$, wherein $R_7$ and $R_8$ are, at each occurrence, independently halogen, haloalkyl, cyano, nitro, $C_1$-$C_{20}$ alkyl, $C_5$-$C_{30}$ aryl, or $C_4$-$C_{30}$ heteroaryl, wherein each $C_1$-$C_{20}$ alkyl, $C_5$-$C_{30}$ aryl, and $C_4$-$C_{30}$ heteroaryl is optionally substituted with at least one substituent selected from the group consisting of cyano, nitro, and halogen, provided that X and Y are not the same; and $Z_1$ and $Z_2$ are each independently $NR_3$, S, or O, wherein $R_3$ is H or an unsubstituted or substituted $C_1$-$C_{20}$ alkyl group.

As used herein, the term "unsubstituted" means that hydrogen atoms are bonded, and in this case, the hydrogen atoms include protium, deuterium, and tritium.

With respect to the term "substituted" as used herein, the substituent may be, for example, a $C_1$-$C_{20}$ alkyl group that is unsubstituted or substituted with a halogen atom, a cyano group, and/or a nitro group; a $C_1$-$C_{20}$ alkoxy group, a halogen atom, a cyano group, or an alkyl halide group (e.g., —$CF_3$) that is unsubstituted or substituted with a halogen atom, a cyano group, and/or a nitro group; a hydroxyl group, a carboxyl group, a carbonyl group, an amine group, a $C_1$-$C_{10}$ alkyl-substituted amine group, a $C_5$-$C_{30}$ aryl-substituted amine group, a $C_4$-$C_{30}$ heteroaryl-substituted amine group, a nitro group, a hydrazyl group, a sulfonic acid group, a $C_1$-$C_{20}$ alkylsilyl group, a $C_1$-$C_{20}$ alkoxysilyl group, a $C_3$-$C_{30}$ cycloalkylsilyl group, a $C_5$-$C_{30}$ arylsilyl group, a $C_4$-$C_{30}$ heteroarylsilyl group, a $C_5$-$C_{30}$ aryl group, or a $C_4$-$C_{30}$ heteroaryl group that is unsubstituted or substituted with a halogen atom, a cyano group, and/or a nitro group; or the like, but the present disclosure is not limited to the above examples.

As used herein, the term "hetero" used in the terms "heteroaromatic ring," "hetero cycloalkylene group," "heteroarylene group," "hetero arylalkylene group," "hetero aryloxylene group," "hetero cycloalkyl group," "heteroaryl group," "heteroarylalkyl group," "heteroaryloxyl group," "heteroaryl amine group," and the like means that at least one, e.g., one to five of carbon atoms constituting such an aromatic or alicyclic ring are substituted with at least one heteroatom selected from the group consisting of N, O, and S.

According to one example embodiment, in Formula 1, when $R_{1a}$, $R_{1b}$, $R_{2a}$, $R_{2b}$, X, and/or Y are/is substituted with an aromatic ring, these aromatic rings may be each independently an unfused or fused aromatic ring such as, but not limited to, an unsubstituted or substituted phenyl group, an unsubstituted or substituted biphenyl group, an unsubstituted or substituted terphenyl group, an unsubstituted or substituted tetraphenyl group, an unsubstituted or substituted naphthyl group, an unsubstituted or substituted anthracenyl group, an unsubstituted or substituted indenyl group, an unsubstituted or substituted phenalenyl group, an unsubstituted or substituted phenanthrenyl group, an unsubstituted or substituted azulenyl group, an unsubstituted or substituted pyrenyl group, an unsubstituted or substituted fluorenyl group, an unsubstituted or substituted tetracenyl group, an unsubstituted or substituted indacenyl group, or an unsubstituted or substituted spirofluorenyl group; and/or an unfused or fused heteroaromatic ring such as a pyrrolyl group, a pyridinyl group, a pyrimidinyl group, a pyrazinyl group, a pyridazinyl group, a triazinyl group, a tetrazinyl group, an imidazolyl group, a pyrazolyl group, an indolyl group, a carbazolyl group, a benzocarbazolyl group, a dibenzocarbazolyl group, an indolocarbazolyl group, an indenocarbazolyl group, a benzofuranocarbazolyl group, a benzothienocarbazolyl group, a quinolinyl group, an isoquinolinyl group, a phthalazinyl group, a quinoxalinyl group, a cinnolinyl group, a quinazolinyl group, a benzoquinolinyl group, a benzoisoquinolinyl group, a benzoquinazolinyl group, a benzonquinoxalinyl group, an acridinyl group, a phenanthrolinyl group, a furanyl group, a pyranyl group, an oxazinyl group, an oxazolyl group, an oxadiazolyl group, a triazolyl group, a dioxynyl group, a benzofuranyl group, a dibenzofuranyl group, a thiopyranyl group, a thiazinyl group, a thiophenyl group, or a N-substituted spirofluorenyl group.

For example, in Formula 1, when $R_{1a}$, $R_{1b}$, $R_{2a}$, $R_{2b}$, X, and/or Y are/is substituted with an aromatic functional group, this functional group may be an aryl group such as a phenyl group, a biphenyl group, a terphenyl group, a naphthyl group, an anthracenyl group, a fluorenyl group, or a spirofluorenyl group that is substituted with at least one functional group selected from a halogen atom such as fluorine, a nitro group, and a cyano group; and/or a heteroaryl group such as a benzothiopheneyl group, a dibenzothiopheneyl group, a benzofuranyl group, a dibenzofuranyl group, a pyrrolyl group, a pyridinyl group, a pyrimidinyl group, a pyrazinyl group, a pyridazinyl group, a triazinyl group, a tetrazinyl group, an imidazolyl group, a pyrazolyl group, an indolyl group, a carbazolyl group, a benzocarbazolyl group, a dibenzocarbazolyl group, an indolocarbazolyl group, an indenocarbazolyl group, a benzofuranocarbazolyl group, a benzothienocarbazolyl group, a quinolinyl group, an isoquinolynyl group, a phthalazinyl group, a quinoxalinyl group, a cinnolinyl group, a quinazolinyl group, a phthalazinyl group, a quinoxalinyl group, a benzoquinolinyl group, a benzoisoquinolinyl group, a benzoquinazolinyl group, or a benzoquinoxalinyl group that is substituted with at least one functional group selected from a halogen atom such as fluorine, a nitro group, and a cyano group.

Since the organic compound of Formula 1 has, as a core, a fused heteroaromatic ring having multiple exocyclic double bonds, the organic compound of Formula 1 has a deep highest occupied molecular orbital (HOMO) energy level. Thus, when the organic compound of Formula 1 is applied to a hole transfer layer of a light-emitting diode, a difference in HOMO energy level between the hole transfer layer and an emitting material layer may be reduced. In addition, the organic compound of Formula 1 is substituted with multiple functional groups with excellent electron withdrawing properties through the exocyclic double bonds, and thus exhibits excellent hole mobility properties. In particular, the organic compound according to the present disclosure is substituted with different functional groups having excellent electron withdrawing properties through each exocyclic double bond, and thus hole mobility properties thereof are further enhanced.

Thus, by applying the organic compound of Formula 1 to a light-emitting diode, balanced numbers of holes and electrons may be injected into an emitting material layer. When the organic compound of Formula 1 is applied to a light-emitting diode, holes and electrons respectively injected from an anode and a cathode may not disappear, but may be injected into an emitting material layer, thereby forming effective excitons, and light emission may be realized in a region where a luminescent material is provided, not at an interface between the emitting material layer and a charge transfer layer adjacent thereto. Accordingly, a light-emitting diode having enhanced luminous efficiency and capable of operating at low voltage may be manufactured using the organic compound of Formula 1.

According to one example embodiment, in Formula 1, when at least one of $R_{1a}$, $R_{1b}$, $R_{2a}$, and $R_{2b}$ is hydrogen, deuterium, or tritium, and when $R_{1a}$, $R_{1b}$, $R_{2a}$, or $R_{2b}$ is not hydrogen, deuterium, or tritium, the other of $R_{1a}$, $R_{1b}$, $R_{2a}$, and $R_{2b}$ may be each independently a $C_5$-$C_{30}$ aryl group substituted with at least one selected from a halogen atom, a cyano group, and a nitro group, or a $C_5$-$C_{30}$ heteroaryl group substituted with at least one selected from a halogen atom, a cyano group, and a nitro group. In some embodiments, $R_{2a}$ and $R_{2b}$ are both hydrogen. In certain embodiments, $R_{1a}$ and $R_{1b}$ are both hydrogen. In other embodiments, $R_{1a}$ and $R_{1b}$ both have the following structure:

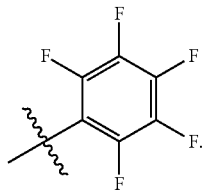 [SMILES: *c1c(F)c(F)c(F)c(F)c1F]

In addition, in some embodiments, X is $CR_5R_6$, wherein $R_5$ may be a halogen atom, a haloalkyl (e.g., —$CF_3$), a cyano group, a nitro group, or a $C_5$-$C_{30}$ aryl group or $C_4$-$C_{30}$ heteroaryl group that is substituted with at least one selected from a cyano group, a nitro group, and a halogen atom, and $R_6$ may be a $C_5$-$C_{30}$ aryl group substituted with at least one selected from a halogen atom, a cyano group, and a nitro group, or a $C_4$-$C_{30}$ heteroaryl group substituted with at least one selected from a halogen atom, a cyano group, and a nitro group. In certain embodiments, $R_5$ and $R_6$ have one of the following structures:

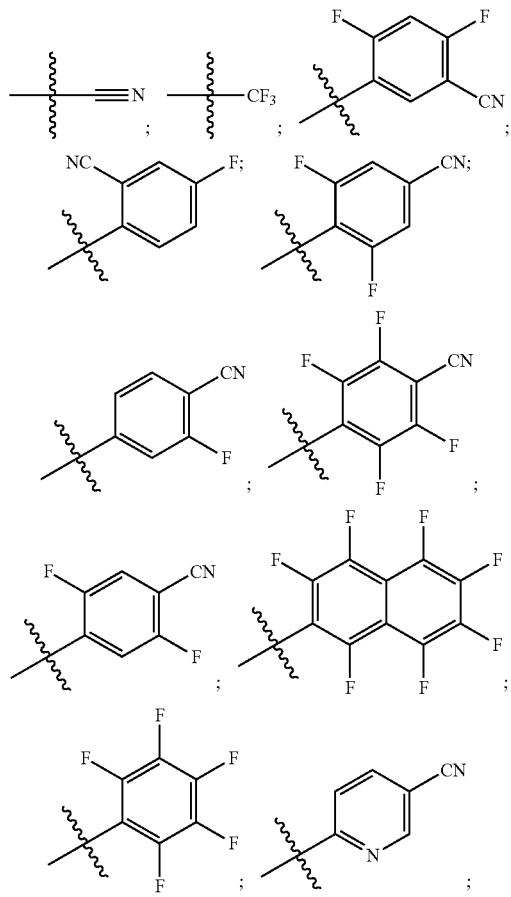

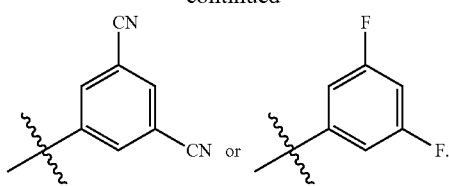

In addition, Y is $CR_7R_8$, wherein $R_7$ and $R_8$ may be each independently a halogen atom, a cyano group, or a nitro group. In some embodiments, $R_7$ and $R_8$ are both cyano.

In some embodiments, $Z_1$ and $Z_2$ are both S.

More particularly, the organic compound that may be used in a hole transfer layer of a light-emitting diode may include any one of organic compounds SH01 to SH13 represented by Formula 2 below, that is, in some embodiments, the compound has one of the following structures (of Formula 2):

Formula 2

SH01

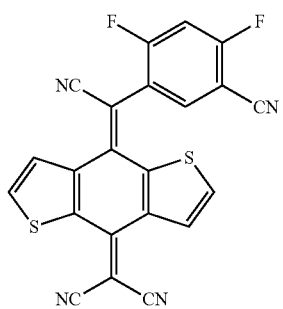

SH02

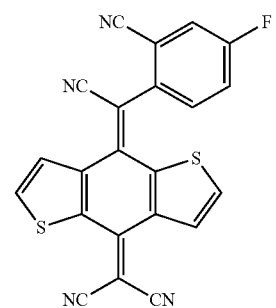

SH03

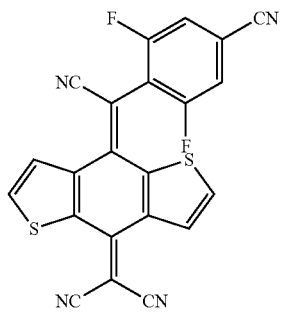

SH04

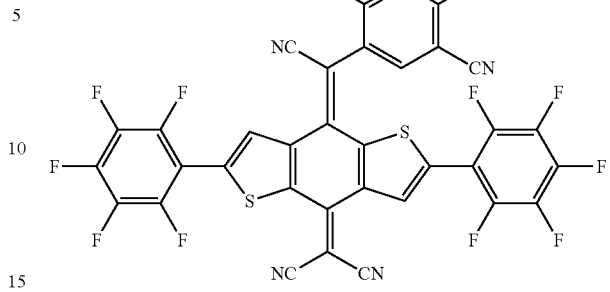

SH05

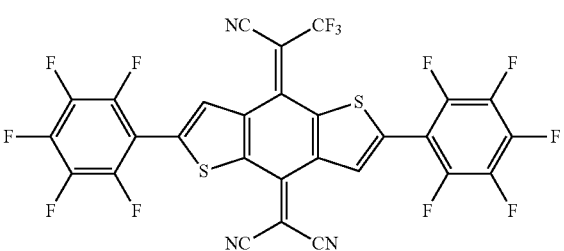

SH06

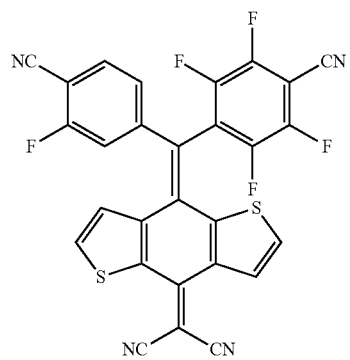

SH07

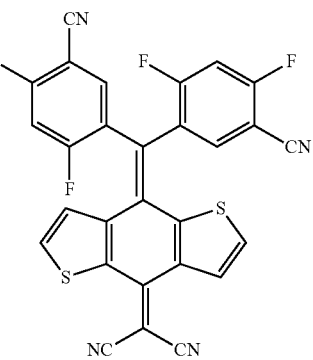

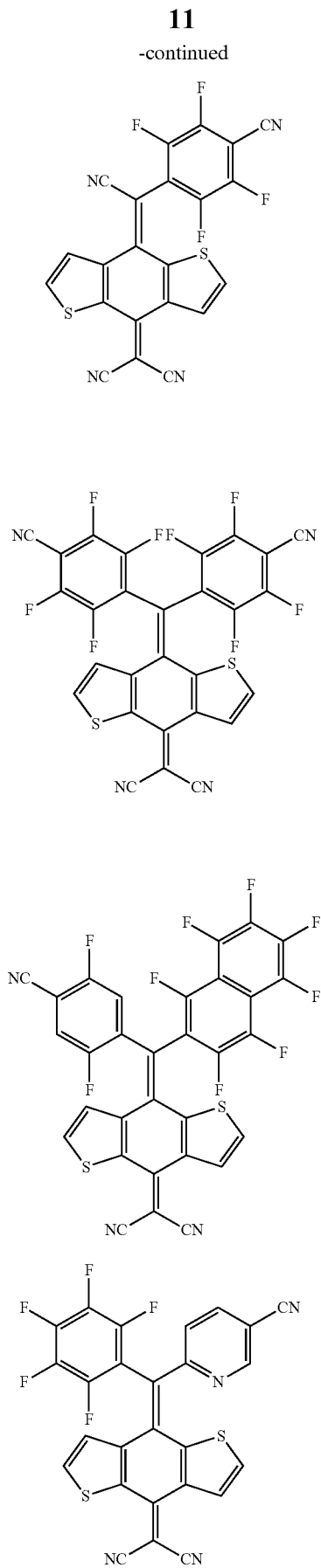

SH08

SH09

SH10

SH011

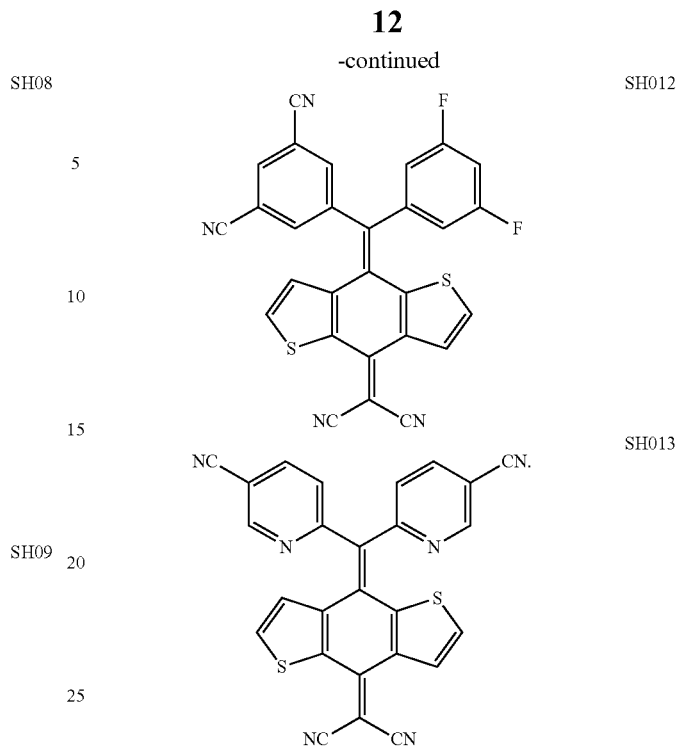

SH012

SH013

The organic compound of Formula 2 has, as a core, a fused heteroaromatic ring having a deep HOMO energy level and exocyclic double bonds, and is substituted with different functional groups having excellent electron withdrawing properties through each exocyclic double bond, thus exhibiting excellent hole mobility properties. Thus, by applying the organic compound of Formula 2 to a hole transfer layer, a light-emitting diode exhibiting excellent luminous efficiency and capable of operating at low voltage may be manufactured. Accordingly, one embodiment provides a light-emitting diode including a compound of any of the foregoing embodiments.

Figure 2:
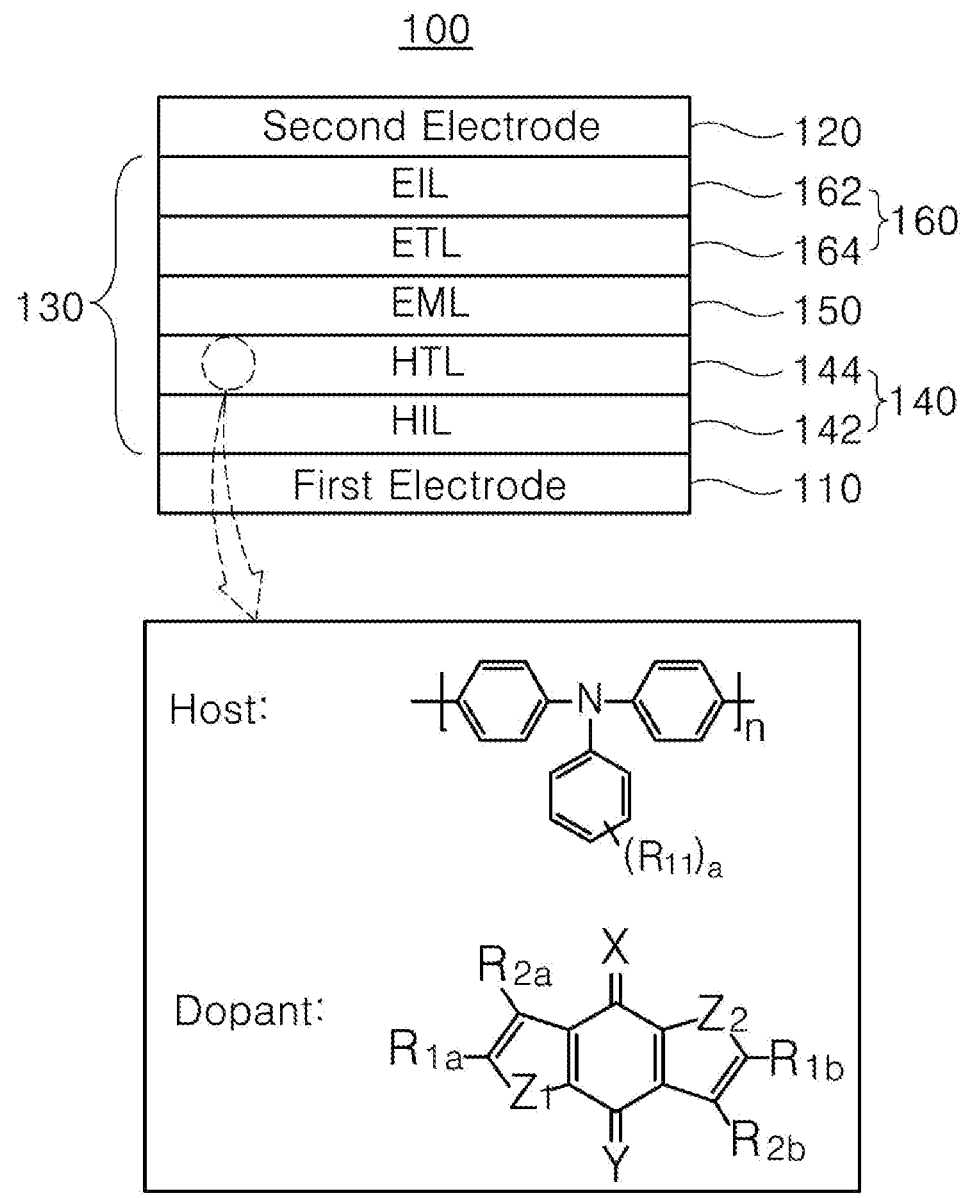
FIG. 2 is a schematic cross-sectional view of a light-emitting diode having a normal structure according to a first example embodiment of the present disclosure.
Figure 3:
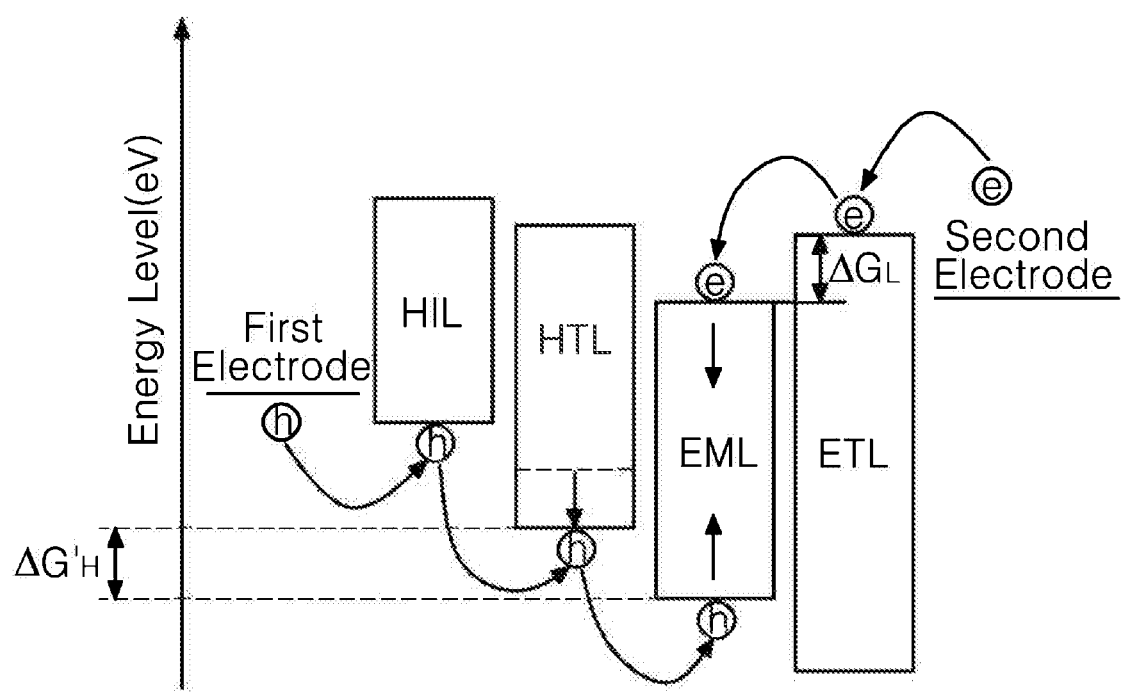
FIG. 3 is a schematic diagram illustrating energy levels of materials constituting electrodes and an emissive layer of the light-emitting diode according to a first example embodiment of the present disclosure.

Hereinafter, a light-emitting diode including the organic compound according to the present disclosure will be described. FIG. 2 is a schematic cross-sectional view of a light-emitting diode 100 having a normal structure according to a first example embodiment of the present disclosure. FIG. 3 is a schematic diagram illustrating bandgap energy levels of materials constituting electrodes and an emissive layer of the light-emitting diode 100 according to a first example embodiment of the present disclosure.

As illustrated in FIG. 2, the light-emitting diode 100 according to an example embodiment of the present disclosure includes a first electrode 110; a second electrode 120 facing the first electrode 110; and an emissive layer 130 disposed between the first electrode 110 and the second electrode 120 and including an emitting material layer (EML) 150. For example, the emissive layer 130 may further include a first charge transfer layer 140 between the first electrode 110 and the EML 150, and a second charge transfer layer 160 between the EML 150 and the second electrode 120.

In the first embodiment of the present disclosure, the first electrode 110 may be an anode such as a hole injection electrode. The first electrode 110 may be provided on a substrate (not shown in FIG. 2) that may be made of glass or a polymer. For example, the first electrode 110 may be made of a doped or undoped metal oxide selected from indium-tin-oxide (ITO), indium-zinc-oxide (IZO), indium-tin-zinc-oxide (ITZO), indium-copper-oxide (ICO), a tin oxide ($SnO_2$), an indium oxide ($In_2O_3$), cadmium:zinc oxide (Cd:ZnO), fluorine:tin oxide (F:$SnO_2$), indium:tin oxide (In:$SnO_2$), gallium:tin oxide (Ga:$SnO_2$), and aluminum:zinc oxide (Al:ZnO; AZO). Optionally, the first electrode 110 may be made of a metal or non-metal material including nickel (Ni), platinum (Pt), gold (Au), silver (Ag), iridium (Ir), or carbon nanotubes (CNTs), other than the above-described metal oxides.

In the first embodiment of the present disclosure, the second electrode 120 may be a cathode such as an electron injection electrode. For example, the second electrode 120 may be made of Ca, Ba, Ca/Al, LiF/Ca, LiF/Al, $BaF_2$/Al, CsF/Al, $CaCO_3$/Al, $BaF_2$/Ca/Al, Al, Mg, Au:Mg, or Ag:Mg. For example, the first electrode 110 and the second electrode 120 may be stacked with a thickness of about 30 nm to about 300 nm.

In one example embodiment, when the light-emitting diode is of a bottom-emission type, the first electrode 110 may be made of a transparent conductive metal such as ITO, IZO, ITZO, or AZO, and for the second electrode 120, Ca, Ba, Ca/Al, LiF/Ca, LiF/Al, $BaF_2$/Al, Al, Mg, an Ag:Mg alloy, or the like may be used.

The first charge transfer layer 140 capable of constituting the emissive layer 130 is disposed between the first electrode 110 and the EML 150. In the first embodiment of the present disclosure, the first charge transfer layer 140 may be a hole transfer layer configured to supply holes to the EML 150. For example, the first charge transfer layer 140 includes a hole injection layer (HIL) 142 and a hole transport layer (HTL) 144 between the first electrode 110 and the EML 150 such that the HIL 142 is disposed adjacent to the first electrode 110 and the HTL 144 is disposed adjacent to the EML 150.

The HIL 142 facilitates injection of holes from the first electrode 110 into the EML 150. For example, the HIL 142 may be formed of an organic material selected from the group consisting of poly(ethylenedioxythiophene):polystyrenesulfonate (PEDOT:PSS), tetrafluoro-tetracyano-quinodimethane ($F_4$-TCNQ)-doped 4,4',4"-tris(diphenylamino) triphenylamine (TDATA), p-doped phthalocyanine such as $F_4$-TCNQ-doped zinc phthalocyanine (ZnPc), $F_4$-TCNQ-doped N,N'-diphenyl-N,N'-bis(1-naphthyl)-1,1'-biphenyl-4,4"-diamine ($\alpha$-NPD), hexaazatriphenylene-hexanitrile (HAT-CN), and a combination thereof, but the present disclosure is not limited thereto. For example, a dopant such as $F_4$-TCNQ may be doped in an amount of about 1 wt % to about 30 wt % with respect to the weight of a host. The HIL 142 may be omitted according to the structure and type of the light-emitting diode 100.

The HTL 144 transports holes from the first electrode 110 to the EML 150. In the drawings, although the first charge transfer layer 140 is illustrated as including the HIL 142 and the HTL 144, the first charge transfer layer 140 may be formed as a single layer. For example, the HIL 142 may be omitted and the first charge transfer layer 140 may be formed of only the HTL 144.

In one example embodiment, the HTL 144 may include the organic compound of Formula 1 or 2.

The organic compound of Formula 1 or 2 has, as a core, a fused heteroaromatic ring and is asymmetrically substituted with functional groups having excellent electron withdrawing properties through multiple exocyclic double bonds. Thus, the organic compound of Formula 1 or 2 has a deep HOMO energy level and strong binding affinity with holes, thus exhibiting excellent hole mobility properties.

Thus, as schematically illustrated in FIG. 3, when the organic compound of Formula 1 or 2 is applied to a hole transfer layer, for example, an HTL, an overall HOMO energy level of the HTL becomes deep, and since a difference ($\Delta G'_H$) in HOMO energy level between the HTL and an EML is significantly reduced, an energy barrier between the HTL and the EML may be removed.

That is, by applying the organic compound of Formula 1 or 2 to an HTL, the difference ($\Delta G'_H$) in HOMO energy level between the HTL and the EML becomes equivalent to, or not significantly different from a difference ($\Delta G_L$) in lowest unoccupied molecular orbital (LUMO) energy level between an electron transport layer (ETL) and the EML.

As such, by using the organic compound of Formula 1 or 2 in an HTL, balanced numbers of holes and electrons are injected into the EML and form excitons, and accordingly, the number of electrons that disappear without forming excitons is reduced or eliminated. In addition, light emission may efficiently occur in a luminescent material injected into the EML, not at an interface between the EML and the HTL or ETL adjacent thereto. Accordingly, the light-emitting diode 100 may exhibit maximized luminous efficiency and operate at low voltage, thus reducing power consumption.

For example, the first charge transfer layer 140 including the HIL 142 and the HTL 144 may be formed using one selected from a vacuum deposition method such as vacuum vapor deposition and sputtering, and a solution process such as spin coating, drop coating, dip coating, spray coating, roll coating, flow coating, casting, screen printing, and inkjet printing; or a combination of these methods. For example, a thickness of the HIL 142 and the HTL 144 may range from about 10 nm to about 200 nm, preferably about 10 nm to about 100 nm, but the present disclosure is not limited thereto.

In one example embodiment, the organic compound of Formula 1 or 2 may be used as a dopant of the HTL 144. At this time, a host of the HTL 144 is not particularly limited, but may be an organic material having a triamine moiety, which has excellent hole mobility. For example, the host of the HTL 144 may include any one of organic materials represented by Formulae 3 to 5 below:

Formula 3

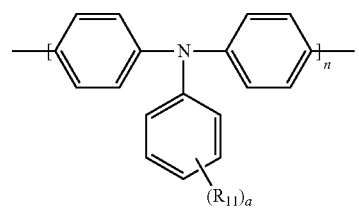

Formula 4

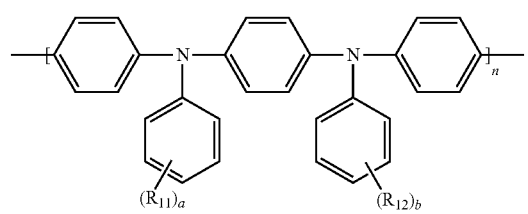

Formula 5

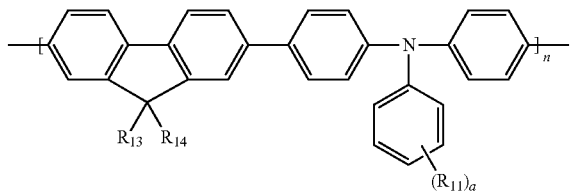

wherein each of $R_{11}$ to $R_{14}$ is independently an unsubstituted or substituted linear or branched $C_1$-$C_{20}$ alkyl group, an unsubstituted or substituted $C_1$-$C_{20}$ alkoxy group, an unsubstituted or substituted $C_5$-$C_{30}$ aryl group, or an unsubstituted or substituted $C_4$-$C_{30}$ heteroaryl group; each of a and b is independently an integer of 1 to 4; and n is an integer of 1 or more.

In a case in which the HTL 144 consists of a host and a dopant, the organic compound of Formula 1 or 2 may be added in an amount of about 1 part by weight to about 200 parts by weight, preferably about 10 parts by weight to about 200 parts by weight, with respect to 100 parts by weight of the host, but the present disclosure is not limited thereto.

In an example embodiment, in Formulae 3 to 5, $R_{11}$ to $R_{14}$ are each independently an unsubstituted or substituted linear or branched $C_1$-$C_{20}$ alkyl group. Examples of the organic compounds of Formulae 3 to 5 include, but are not limited to, poly[N,N'-bis(4-butylphenyl)-N,N'-bis(phenyl)-benzidine] (poly-TPD; p-TPD), poly[(9,9-dioctylflorenyl-2,7-diyl)-co-(4,4'-(N-(4-sec-butylphenyl)diphenylamine)] (TFB), poly[(9,9-dioctylflorenyl-2,7-diyl)-co-(4,4'-(N-(p-butylphenyl)diphenylamine))], poly[bis(4-phenyl)(2,4,6-trimethylphenyl)amine] (PTAA), N,N'-bis(3-methylphenyl)-N,N'-bis(phenyl)benzidine (TPD), N,N'-bis(4-methylphenyl)-N,N'-bis(phenyl)benzidine), $N^1,N^4$-diphenyl-$N^1,N^4$-di-m-tolylbenzene-1,4-diamine (TTP), N,N,N',N'-tetra(3-methylphenyl)3,3'-dimethylbenzidien (HMTPD), di-[4-(N,N'-di-p-tolyl-amino)-phenyl]cyclohexane (TAPC), N4,N4'-Bis(4-(6-((3-ethyloxetan-3-yl)methoxy)hexyl)phenyl)-N4,N4'-diphenylbiphenyl-4,4'-diamine (OTPD), and 4,4',4''-tris(N,N-phenyl-3-methylphenylamino)triphenylamine.

In this regard, the HTL 144 may use a polymer as a host and the organic compound of Formula 1 or 2 as a dopant. In this case, the HTL 144 may have enhanced hole mobility properties and a reduced HOMO energy level (deep HOMO energy level), and accordingly, a HOMO energy barrier between the HTL 144 and the EML 150 may be reduced or removed.

Meanwhile, the EML 150 may be formed of inorganic luminescent particles or an organic luminescent material. When the EML 150 is formed of inorganic luminescent particles, the inorganic luminescent particles may be inorganic luminescent nanoparticles such as quantum dots (QDs) or quantum rods (QRs).

QDs or QRs are inorganic particles that emit light while electrons in an unstable state drop from a conduction band to a valence band. These inorganic luminescent nanoparticles have a very high extinction coefficient and exhibit an excellent quantum yield among inorganic particles, and thus emit strong fluorescence. In addition, since a luminescence wavelength varies according to the size of inorganic luminescent nanoparticles, when the size of inorganic luminescent nanoparticles is appropriately adjusted, light in the entire visible light region may be obtained, thus realizing a variety of colors. That is, when inorganic luminescent nanoparticles such as QDs or QRs are used as a luminescent material of the EML 150, color purity of individual pixels may be enhanced, and white light consisting of red (R), green (G), and blue (B) light with high purity may also be realized.

In one example embodiment, the QDs or the QRs may have a single structure. In another example embodiment, the QDs or the QRs may have a heterologous structure including a core and a shell. In this case, the shell may be formed as a single shell or multi-shells.

A growth degree, a crystal structure, and the like of these inorganic luminescent nanoparticles may be adjusted according to the reactivity and injection rate of a reactive precursor constituting a core and/or a shell, the type of ligand, a reaction temperature, and the like, and accordingly, light emission at various wavelengths may be induced by adjusting energy bandgaps.

For example, the QDs or the QRs may have a heterologous structure including: a core provided at a central portion thereof and configured to emit light; and a shell covering a surface of the core to protect the core, and a ligand component for dispersing the QDs or the QRs in a solvent may cover a surface of the shell. For example, the QDs or the QRs may have a type-I core/shell structure in which electrons and holes move towards the core and are recombined in the core, and as a result, energy is emitted as light, as a structure in which the energy bandgap of a component constituting the core is covered by the energy bandgap of the shell.

In a case in which the QDs or the QRs have a type-I core/shell structure, the core is a portion in which light emission substantially occurs, and the luminescence wavelength of the QDs or the QRs is determined according to the size of core. To achieve a quantum confinement effect, it is necessary for the core to have a size smaller than an exciton Bohr radius according to each material, and have an optical bandgap in the corresponding size.

Meanwhile, the shell of the QDs or the QRs promotes a quantum confinement effect of the core and determines the stability of the QDs or the QRs. Unlike internal atoms, atoms that appear on surfaces of colloidal QDs or QRs having a single structure have lone pair electrons that do not participate in chemical bonding. The energy level of these surface atoms is between a conduction band edge and a valence band edge of the QDs or the QRs, and thus charges may be trapped, resulting in formation of surface defects. Luminous efficiency of the QDs or the QRs may be reduced due to a non-radiative recombination process of excitons which results from the surface defects, and the trapped charges react with external oxygen and a compound and thus may cause modification of a chemical composition of the QDs or the QRs, or electric/optical properties of the QDs or the QRs may be permanently lost.

Thus, in one example embodiment, the QDs or the QRs may have a heterologous structure including a core and a shell. In order for the shell to be efficiently formed on a surface of the core, a lattice constant of a material constituting the shell should be similar to that of a material constituting the core. By covering the surface of the core with the shell, oxidation of the core is prevented and thus chemical stability of the QDs or the QRs may be enhanced, loss of excitons due to surface trapping at the surface of the core may be minimized, and energy loss due to molecular vibration may be prevented, resulting in enhancement of quantum efficiency.

The QDs or the QRs may be semiconductor nanocrystals or metal oxide particles having a quantum confinement effect. For example, the QDs or the QRs may include Group II-IV, III-V, IV-VI, or I-III-VI compound semiconductor nanocrystals. More particularly, cores and/or shells constituting the QDs or the QRs may be Group II-VI compound semiconductor nanocrystals such as CdS, CdSe, CdTe, ZnS, ZnSe, ZnTe, HgS, HgTe, and/or a combination thereof; Group III-V compound semiconductor nanocrystals such as GaP, GaAs, GaSb, InP, InAs, InSb, and/or a combination thereof; Group IV-VI compound semiconductor nanocrystals such as PbS, PbSe, PbTe, and/or a combination thereof; Group I-III-VI compound semiconductor nanocrystals such as $AgGaS_2$, $AgGaSe_2$, $AgGaTe_2$, $CuInS_2$, $CuInSe_2$, $CuGaS_2$, $CuGaSe_2$, and/or a combination thereof; metal oxide nanoparticles such as ZnO, $TiO_2$, and/or a combination thereof; or core-shell structured nanocrystals such as CdSe/ZnSe, CdSe/ZnS, CdS/ZnSe, CdS/ZnS, ZnSe/ZnS, InP/ZnS, ZnO/MgO, and/or a combination thereof. Semiconductor nanoparticles may be undoped or doped with a rare earth element such as europium (Eu), erbium (Er), terbium (Tb), thulium (Tm), or dysprosium (Dy), or a combination thereof, or may be doped with a transition metal element such as manganese (Mn), copper (Cu), silver (Ag), or aluminum (Al), or a combination thereof.

For example, cores constituting the QDs or the QRs may be selected from the group consisting of ZnSe, ZnTe, CdSe, CdTe, InP, ZnCdS, $Cu_xIn_{1-x}S$, $Cu_xIn_{1-x}Se$, $Ag_xIn_{1-x}S$, and a combination thereof. In addition, shells constituting the QDs or the QRs may be selected from the group consisting of ZnS, GaP, CdS, ZnSe, CdS/ZnS, ZnSe/ZnS, ZnS/ZnSe/CdSe, GaP/ZnS, CdS/CdZnS/ZnS, ZnS/CdSZnS, $Cd_xZn_{1-x}S$, and a combination thereof.

Meanwhile, the QDs may be alloy QDs (e.g., $CdS_xSe_{1-x}$, $CdSe_xTe_{1-x}$, and $Zn_xCd_{1-x}Se$) such as homogeneous alloy QDs or gradient alloy QDs.

When the EML 150 is formed of inorganic luminescent particles such as QDs or QRs, a solution including QDs or QRs in a solvent is applied to the first charge transfer layer 140, for example, the HTL 144, and then the solvent is volatilized, thereby forming the EML 150.

In one example embodiment, the EML 150 may be formed by coating (e.g., a solution process) the first charge transfer layer 140 with a dispersion including QDs or QRs, which are luminescent nanoparticles, in a solvent and volatilizing the solvent. The EML 150 may be formed using one solution process selected from spin coating, drop coating, dip coating, spray coating, roll coating, flow coating, casting, screen printing, and inkjet printing; or a combination thereof.

In one example embodiment, the EML 150 may include QDs or QRs, which are inorganic luminescent nanoparticles having photoluminescence (PL) emission properties at 440 nm, 530 nm, and 620 nm, and thus the manufacture of a white light-emitting diode is enabled. Optionally, the EML 150 may include QDs or QRs, which are luminescent nanoparticles having any one of a red color, a green color, and a blue color, and may be formed such that the EML 150 individually emits light of any one color.

In other embodiments, the EML 150 may be formed of an organic luminescent material. The organic luminescent material of the EML 150 is not particularly limited as long as it is a generally used organic luminescent material. For example, the EML 150 may be formed of an organic luminescent material that emits red light, green light, and/or blue light, and may include a fluorescent material or a phosphorescent material. In addition, the organic luminescent material of the EML 150 may include a host and a dopant. When the organic luminescent material consists of a host-dopant system, the dopant may be doped in an amount of about 1 wt % to about 50 wt %, preferably about 1 wt % to about 30 wt %, with respect to the weight of the host, but the present disclosure is not limited to the above example.

An organic host used in the EML 150 is not particularly limited as long as it is a commonly used material. For example, the organic host used in the EML 150 may be tris(8-hydroxyquinoline)aluminum ($Alq_3$), TCTA, PVK, 4,4'-bis(N-carbazolyl)-1,1'-biphenyl (CBP), 4,4'-bis(9-carbazolyl)-2,2'-dimethylbiphenyl (CDBP), 9,10-di(naphthalene-2-yl)anthracene (ADN), 3-tert-butyl-9,10-di(naphtha-2-yl)anthracene (TBADN), 2-methyl-9,10-bis(naphthalene-2-yl)anthracene (MADN), 1,3,5-tris(N-phenylbenzimidazole-2-yl)benzene (TPBi), distyrylarylene (DSA), mCP, 1,3,5-tris(carbazol-9-yl)benzene (TCP), or the like.

When the EML 150 emits red light, the dopant included in the EML 150 may be an organic compound or an organic metal complex such as 5,6,11,12-tetraphenylnaphthalene (Rubrene), bis(2-benzo[b]-thiophene-2-yl-pyridine)(acetylacetonate)iridium(III) ($Ir(btp)_2(acac)$), bis[1-(9,9-diemthyl-9H-fluorn-2-yl)-isoquinoline](acetylacetonate)iridium(III) ($Ir(fliq)_2(acac)$), bis[2-(9,9-diemthyl-9H-fluorn-2-yl)-quinoline](acetylacetonate)iridium(III) ($Ir(flq)_2(acac)$), bis-(2-phenylquinoline)(2-(3-methylphenyl)pyridinate)irideium (III) ($Ir(phq)_2typ$), or iridium(III)bis(2-(2,4-difluorophenyl)quinoline)picolinate (FPQIrpic), but the present disclosure is not limited to the above examples.

When the EML 150 emits green light, the dopant included in the EML 150 may be an organic compound or an organic metal complex such as N,N'-dimethyl-quinacridone (DMQA), coumarin 6,9,10-bis[N,N-di-(p-tolyl)amino]anthracene (TTPA), 9,10-bis[phenyl(m-tolyl)-amino]anthracene (TPA), bis(2-phenylpyridine)(acetylacetonate)iridium (III) ($Ir(ppy)_2(acac)$), fac-tris(phenylpyridine)iridium(III) ($fac-Ir(ppy)_3$), or tris[2-(p-tolyl)pyridine]iridium(III) ($Ir(m-ppy)_3$), but the present disclosure is not limited to the above examples.

When the EML 150 emits blue light, the dopant included in the EML 150 may be an organic compound or an organic metal complex such as 4,4'-bis[4-(di-p-tolylamino)styryl]biphenyl (DPAVBi), perylene, 2,5,8,11-tetra-tert-butylpherylene (TBPe), bis(3,5-difluoro-2-(2-pyridyl)phenyl-(2-carbozylpyridyl)iridium(III) (FirPic), mer-tris(1-phenyl-3-methylimidazolin-2-ylidene-C,C2')iridium(III) ($mer-Ir(pmi)_3$), or tris(2-(4,6-difluorophenyl)pyridine)iridium(III) ($Ir(Fppy)_3$), but the present disclosure is not limited to the above examples.

When the EML 150 is formed of an organic luminescent material, the EML 150 may be formed using one selected from a vacuum deposition process including vacuum vapor deposition and sputtering, and a solution process such as spin coating, drop coating, dip coating, spray coating, roll coating, flow coating, casting, screen printing, and inkjet printing; or a combination of these processes.

Meanwhile, the second charge transfer layer 160 is located between the EML 150 and the second electrode 120. In the present embodiment, the second charge transfer layer 160 may be an ETL that supplies electrons to the EML 150. In one example embodiment, the second charge transfer layer 160 includes an electron injection layer (EIL) 162 between the second electrode 120 and the EML 150 such that the EIL 162 is arranged adjacent to the second electrode 120, and an electron transport layer (ETL) 164 between the second electrode 120 and the EML 150 such that the ETL 164 is arranged adjacent to the EML 150.

The EIL 162 facilitates injection of electrons from the second electrode 120 into the EML 150. For example, the EIL 162 may be formed of a material obtained by doping a metal such as aluminum (Al), cadmium (Cd), cesium (Cs), copper (Cu), gallium (Ga), germanium (Ge), indium (In), or lithium (Li) with fluorine or binding such a metal to fluorine; or a metal oxide such as titanium dioxide ($TiO_2$), zinc oxide (ZnO), zirconium oxide (ZrO), tin oxide ($SnO_2$), tungsten oxide ($WO_3$), or tantalum oxide ($Ta_2O_3$) that is undoped or doped with Al, magnesium (Mg), In, Li, Ga, Cd, Cs, Cu, or the like.

The ETL 164 transports electrons to the EML 150. The ETL 164 may be formed of an inorganic material and/or an organic material. In a case in which the ETL 164 is formed of an inorganic material, the ETL 164 may be formed of an inorganic material selected from the group consisting of metal/non-metal oxides such as titanium dioxide ($TiO_2$), zinc oxide (ZnO), zinc magnesium oxide (ZnMgO), zirconium oxide (ZrO), tin oxide ($SnO_2$), tungsten oxide ($WO_3$), tantalum oxide ($Ta_2O_3$), hafnium oxide ($HfO_3$), aluminum oxide ($Al_2O_3$), zirconium silicon oxide ($ZrSiO_4$), barium titanium oxide ($BaTiO_3$), and barium zirconium oxide ($BaZrO_3$) that are undoped or doped with Al, Mg, In, Li, Ga, Cd, Cs, Cu, or the like; semiconductor particles such as CdS, ZnSe, and ZnS that are undoped or doped with Al, Mg, In, Li, Ga, Cd, Cs, Cu, or the like; a nitride such as $Si_3N_4$; and a combination thereof.

In a case in which the ETL 164 is formed of an organic material, for the ETL 164, an organic material such as an oxazole-based compound, an isoxazole-based compound, a triazole-based compound, an isothiazole-based compound, an oxadiazole-based compound, a thiadiazole-based compound, a phenanthroline-based compound, a perylene-based compound, a benzoxazole-based compound, a benzothiazole-based compound, a benzimidazole-based compound, a triazine-based compound, or an aluminum complex may be used. In particular, an organic material that may constitute the ETL 164 may be selected from the group consisting of 3-(biphenyl-4-yl)-5-(4-tertbutylphenyl)-4-phenyl-4H-1,2,4-triazole (TAZ), 2,9-dimethyl-4,7-diphenyl-1,10-phenanthroline (bathocuproine; BCP), 2,2',2"-(1,3,5-benzinetriyl)-tris (1-phenyl-1-H-benzimidazole) (TPBi), 2-[4-(9,10-di-2-naphthalenyl-2-anthracenyl)phenyl]-1-phenyl-1H-benzimidazole, tris(8-hydroxyquinoline)aluminum ($Alq_3$), bis(2-methyl-8-quninolinato)-4-phenylphenolatealuminum (III) (Balq), bis(2-methyl-quninolinato)(triphenylsiloxy), 8-hydroxy-quinolinato lithium (Liq), bis(2-methyl-quinolinato)(tripnehylsiloxy)aluminum (III) (Salq), and a combination thereof, but the present disclosure is not limited to the above examples.

Similar to the first charge transfer layer 140, although FIG. 2 illustrates the second charge transfer layer 160 as two layers including the EIL 162 and the ETL 164, the second charge transfer layer 160 may be formed only as a single layer of the ETL 164. In addition, the second charge transfer layer 160 may be formed as a single layer of the ETL 164 using a blend of an electron-transporting material such as the above-described inorganic materials and cesium carbonate.

The second charge transfer layer 160 including the EIL 162 and/or the ETL 164 may be formed using one solution process selected from spin coating, drop coating, dip coating, spray coating, roll coating, flow coating, casting, screen printing, and inkjet printing; or a combination thereof. For example, the EIL 162 and the ETL 164 may be stacked to a thickness of about 10 nm to about 200 nm, preferably, about 10 nm to about 100 nm.

For example, in a case in which a mixed charge transfer layer (CTL) configured such that the HTL 144 constituting the first charge transfer layer 140 is formed of an organic material and the second charge transfer layer 140 is formed of an inorganic material is introduced, luminescence characteristics of the light-emitting diode 100 may be enhanced.

Meanwhile, in a case in which holes pass through the EML 150 and are transferred to the second electrode 120, or electrons pass through the EML 150 and are transferred to the first electrode 120, the lifespan and efficiency of a device may be reduced. To prevent this, the light-emitting diode 100 according to a first embodiment of the present disclosure may include at least one exciton blocking layer adjacent to the EML 150.

For example, the light-emitting diode 100 according to a first embodiment of the present disclosure may include an electron blocking layer (EBL) capable of controlling and preventing transfer of electrons, between the HTL 144 and the EML 150.

For example, the EBL may be formed of TCTA, tris[4-(diethylamino)phenyl]amine), N-(biphenyl-4-yl)-9,9-dimethyl-N-(4-(9-phenyl-9H-carbazole-3-yl)phenyl)-9H-fluorene-2-amine, tri-p-tolylamine, 1,1-bis(4-(N,N'-di(ptolyl) amino)phenyl)cyclohexane (TAPC), m-MTDATA, 1,3-bis (N-carbazolyl)benzene (mCP), 3,3'-bis(N-carbazolyl)-1,1'-biphenyl (mCBP), Poly-TPD, copper phthalocyanine (CuPc), DNTPD, and/or 1,3,5-tris[4-(diphenylamino)phenyl]benzene (TDAPB).

In addition, a hole blocking layer (HBL) as a second exciton blocking layer is located between the EML 150 and the ETL 164, and thus may prevent transfer of holes between the EML 150 and the ETL 164. In one example embodiment, a material for forming the HBL may be an organic derivative such as an oxadiazole-based compound, a triazole-based compound, a phenanthroline-based compound, a benzoxazole-based compound, a benzothiazole-based compound, a benzimidazole-based compound, a triazine-based compound, or the like that may be used in the ETL 164.

For example, the HBL may be formed of 2,9-dimethyl-4,7-diphenyl-1,10-phenanthroline (BCP), BAlq, $Alq_3$, PBD, spiro-PBD, and/or Liq, which have/has a deeper highest occupied molecular orbital (HOMO) energy level than that of a material used in the EML 150.

As described above, according to the first embodiment of the present disclosure, the organic compound of Formula 1 or 2 is included in the HTL 144 located between the first electrode 110 and the EML 150. The organic compound of Formula 1 or 2 is configured such that different types of electron withdrawing functional groups are bound to a heteroaromatic ring as a core via each of multiple exocyclic double bonds, and thus has a deep HOMO energy level and excellent hole mobility properties. A HOMO energy barrier between the HTL 144 and the EML 150 is reduced by reducing the HOMO energy level of the HTL 144. Since balanced numbers of holes and electrons are injected into the EML 150, luminous efficiency of the light-emitting diode 100 may be enhanced and the light-emitting diode 100 may operate at a low voltage, thus reducing power consumption.

Figure 4:
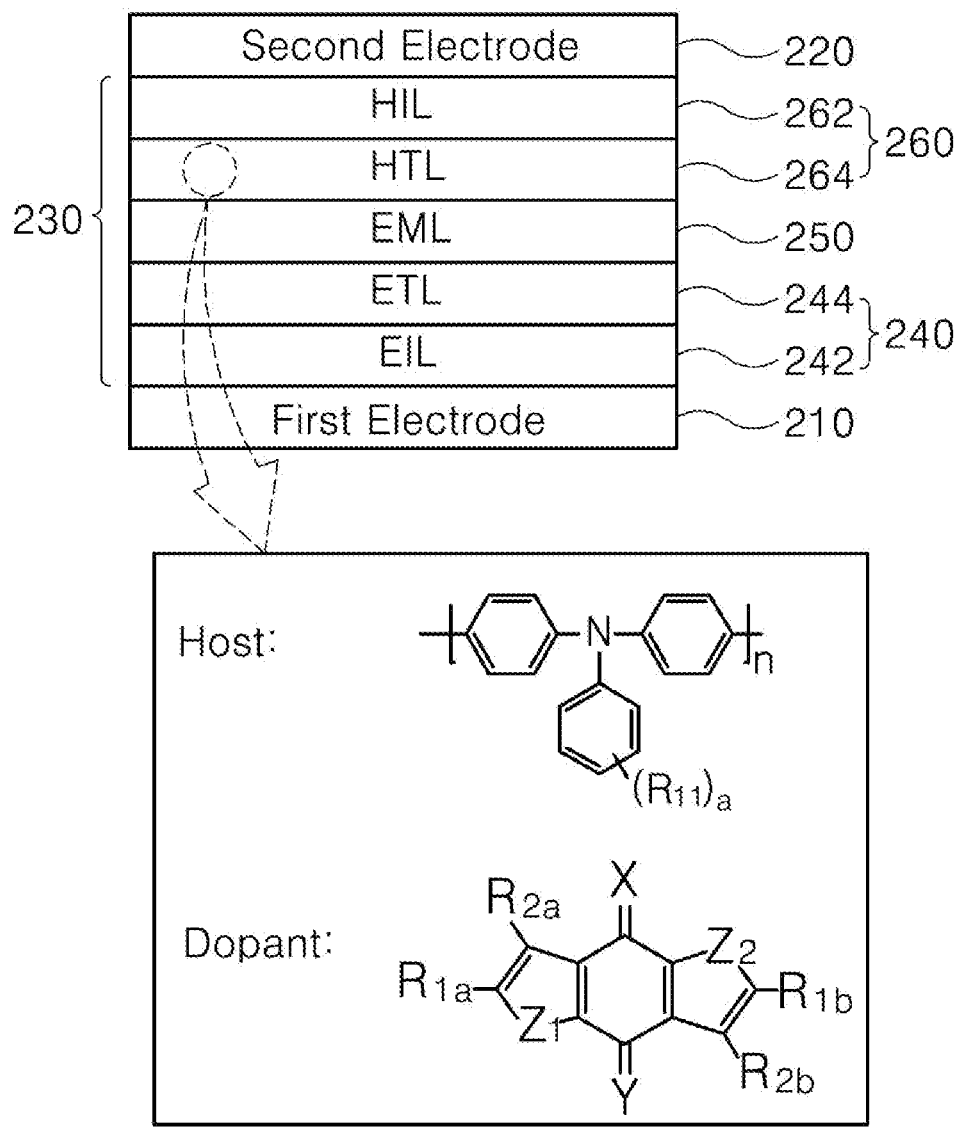
FIG. 4 is a schematic cross-sectional view of a light-emitting diode having an inverted structure according to a second example embodiment of the present disclosure.
Figure 5:
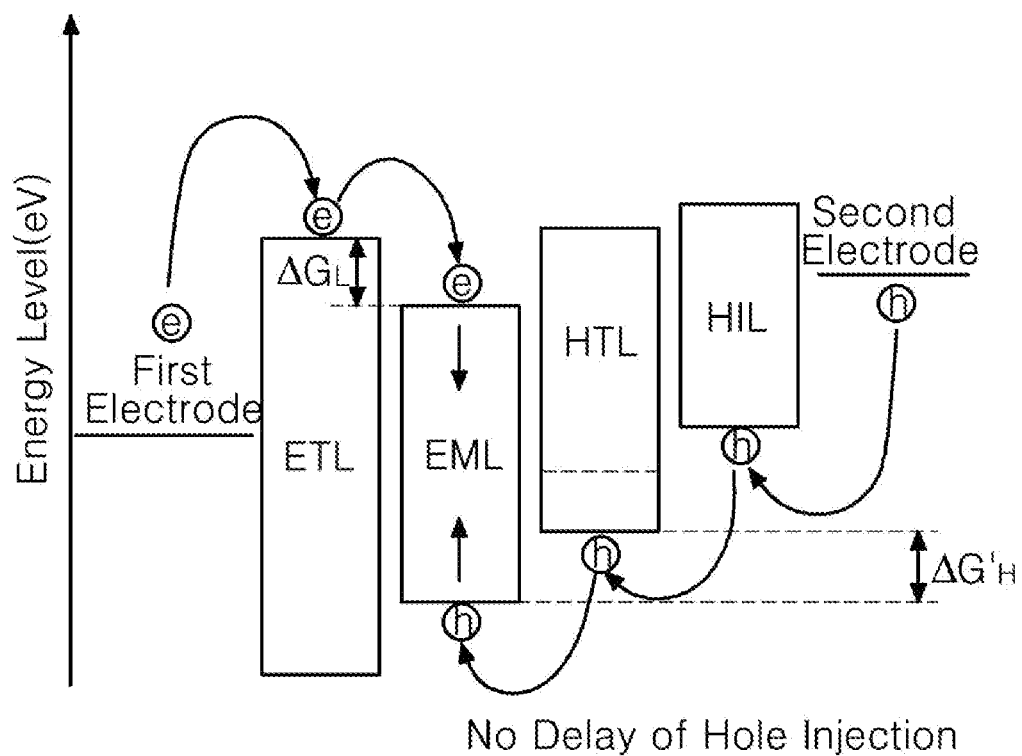
FIG. 5 is a schematic diagram illustrating energy levels of materials constituting electrodes and an emissive layer of the light-emitting diode according to a second embodiment of the present disclosure.

Meanwhile, the case of a light-emitting diode having a normal structure such that an HTL is located between a first electrode having a relatively low work function and an EML, and an ETL is located between a second electrode having a relatively high work function and the EML has been described with reference to FIGS. 2 and 3. The light-emitting diode may have an inverted structure, not the normal structure, and this case will be described below. FIG. 4 is a schematic cross-sectional view of a light-emitting diode 200 having an inverted structure according to a second embodiment of the present disclosure. FIG. 5 is a schematic diagram illustrating energy levels of materials constituting electrodes and an emissive layer of the light-emitting diode 200 according to a second embodiment of the present disclosure.

As illustrated in FIG. 4, the light-emitting diode 200 according to a second embodiment of the present disclosure includes a first electrode 210, a second electrode 220 facing the first electrode 210, and an emissive layer 230 between the first electrode 210 and the second electrode 220 and including an EML 250. The emissive layer 230 may further include a first charge transfer layer 240 between the first electrode 210 and the EML 250, and a second charge transfer layer 260 between the second electrode 220 and the EML 250.

In the second embodiment of the present disclosure, the first electrode 210 may be a cathode such as an electron injection electrode. For example, the first electrode 210 may be made of a doped or undoped metal oxide such as ITO, IZO, ITZO, ICO, $SnO_2$, $In_2O_3$, Cd:ZnO, F:$SnO_2$, In:$SnO_2$, Ga:$SnO_2$, or AZO; or, other than the above-described metal oxides, a material including nickel (Ni), platinum (Pt), gold (Au), silver (Ag), iridium (Ir), or carbon nanotubes.

In the second embodiment of the present disclosure, the second electrode 220 may be an anode such as a hole injection electrode. For example, the second electrode 220 may be made of Ca, Ba, Ca/Al, LiF/Ca, LiF/Al, $BaF_2$/Al, CsF/Al, $CaCO_3$/Al, $BaF_2$/Ca/Al, Al, Mg, Au:Mg, or Ag:Mg. For example, the first electrode 210 and the second electrode 220 may be stacked to a thickness of 30 nm to 300 nm.

In the second embodiment of the present disclosure, the first charge transfer layer 240 may be an electron transfer layer that supplies electrons to the EML 250. In one example embodiment, the first charge transfer layer 240 includes an EIL 242 between the first electrode 210 and the EML 250 such that the EIL 242 is located adjacent to the first electrode 210, and an ETL 244 between the first electrode 210 and the EML 250 such that the ETL 244 is located adjacent to the EML 250.

The EIL 242 may be formed of a material obtained by doping a metal such as Al, Cd, Cs, Cu, Ga, Ge, In, or Li with fluorine or binding such a metal to fluorine; or a metal oxide such as $TiO_2$, ZnO, ZrO, $SnO_2$, $WO_3$, or $Ta_2O_3$ that is undoped or doped with Al, Mg, In, Li, Ga, Cd, Cs, Cu, or the like.

The ETL 244 may be formed of an inorganic material and/or an organic material. In a case in which the ETL 244 is formed of an inorganic material, the ETL 244 may be formed of an inorganic material selected from the group consisting of metal/non-metal oxides such as $TiO_2$, ZnO, ZnMgO, ZrO, $SnO_2$, $WO_3$, $Ta_2O_3$, $HfO_3$, $Al_2O_3$, $ZrSiO_4$, $BaTiO_3$, and $BaZrO_3$ that are undoped or doped with Al, Mg, In, Li, Ga, Cd, Cs, Cu, or the like; semiconductor particles such as CdS, ZnSe, and ZnS that are undoped or doped with Al, Mg, In, Li, Ga, Cd, Cs, Cu, or the like; a nitride such as $Si_3N_4$; and a combination thereof.

In a case in which the ETL 244 is formed of an organic material, for the ETL 244, an oxazole-based compound, an isoxazole-based compound, a triazole-based compound, an isothiazole-based compound, an oxadiazole-based compound, a thiadiazole-based compound, a perylene-based compound, or an aluminum complex may be used. In particular, an organic material that may constitute the ETL 244 may be selected from the group consisting of TAZ, BCP, TPBi, 2-[4-(9,10-di-2-naphthalenyl-2-anthracenyl)phenyl]-1-phenyl-1H-benzimidazole, Alq3, Balq, LIQ, Salq, and a combination thereof, but the present disclosure is not limited to the above examples.

Meanwhile, the first charge transfer layer 240 may be formed only as a single layer of the ETL 244. In addition, the first charge transfer layer 240 may be formed as a single layer of the ETL 244 using a blend of an electron-transporting material such as the above-described inorganic particles and cesium carbonate. For example, the EIL 242 and the ETL 244 may be stacked to a thickness of 10 nm to 200 nm, preferably 10 nm to 100 nm.

The EML 250 may be formed of inorganic luminescent particles or an organic luminescent material. The inorganic luminescent particles may be inorganic luminescent nanoparticles such as QDs or QRs. QDs or QRs may have a single structure, or a heterologous structure including a core/a shell.

The QDs or the QRs may be semiconductor nanocrystals or metal oxide particles having a quantum confinement effect. For example, the QDs or the QRs may include Group II-IV, III-V, IV-VI, or I-III-VI compound semiconductor nanocrystals. More particularly, cores and/or shells constituting the QDs or the QRs may be Group II-VI compound semiconductor nanocrystals such as CdS, CdSe, CdTe, ZnS, ZnSe, ZnTe, HgS, HgTe, and/or a combination thereof; Group III-V compound semiconductor nanocrystals such as GaP, GaAs, GaSb, InP, InAs, InSb, and/or a combination thereof; Group IV-VI compound semiconductor nanocrystals such as PbS, PbSe, PbTe, and/or a combination thereof; Group I-III-VI compound semiconductor nanocrystals such as $AgGaS_2$, $AgGaSe_2$, $AgGaTe_2$, $CuInS_2$, $CuInSe_2$, $CuGaS_2$, $CuGaSe_2$, and/or a combination thereof; metal oxide nanoparticles such as ZnO, $TiO_2$, and/or a combination thereof; or core-shell structured nanocrystals such as CdSe/ZnSe, CdSe/ZnS, CdS/ZnSe, CdS/ZnS, ZnSe/ZnS, InP/ZnS, ZnO/MgO, and/or a combination thereof. Semiconductor nanoparticles may be undoped or doped with a rare earth element such as Eu, Er, Tb, Tm, or Dy, or a combination thereof, or may be doped with a transition metal element such as Mn, Cu, Ag, or Al, or a combination thereof.

In a case in which the EML 250 is formed of inorganic luminescent particles such as QDs or QRs, a solution including QDs or QRs in a solvent is applied to the first charge transfer layer 240, e.g., the ETL 244, and then the solvent is volatilized, thereby forming the EML 250.

In a case in which the EML 250 is formed of an organic luminescent material, the EML 250 may be formed of an organic luminescent material that emits red light, green light, and/or blue light, and may include a fluorescent material or a phosphorescent material. In addition, the organic luminescent material of the EML 250 may include a host and a dopant. When the organic luminescent material consists of a host-dopant system, the dopant may be doped in an amount of about 1 wt % to about 50 wt %, preferably about 1 wt % to about 30 wt %, with respect to a weight of the host, but the present disclosure is not limited thereto.

In a case in which the EML 250 is formed of an organic luminescent material, the EML 250 may be formed using one selected from a vacuum deposition process including vacuum vapor deposition and sputtering, and a solution process such as spin coating, drop coating, dip coating, spray coating, roll coating, flow coating, casting, screen printing, and inkjet printing; or a combination thereof.

Meanwhile, in the second embodiment of the present disclosure, the second charge transfer layer 260 may be a hole transfer layer that supplies holes to the EML 250. In one example embodiment, the second charge transfer layer 260 includes a HIL 262 between the second electrode 220 and the EML 250 such that the HIL 262 is located adjacent to the second electrode 220, and an HTL 264 between the second electrode 220 and the EML 250 such that the HTL 264 is located adjacent to the EML 250.

The HIL 262 may be formed of a material selected from PEDOT:PSS, F4-TCNQ-doped TDATA, p-doped phthalocyanine such as F4-TCNQ-doped ZnPc, F4-TCNQ-doped α-NPD, HAT-CN, and a combination thereof, but the present disclosure is not limited to the above examples. For example, a dopant such as $F_4$-TCNQ may be doped in an amount of about 1 wt % to about 30 wt % with respect to the weight of a host. The HIL 262 may be omitted according to the structure and type of the light-emitting diode 200.

The HTL 264 includes the organic compound of Formula 1 or 2. For example, the organic compound of Formula 1 or 2 may be used as a dopant of the HTL 264, and in this case, the HTL 264 may use, as a host, an organic material having a triphenylamine moiety, e.g., the above-described organic materials of Formulae 3 to 5.

The second charge transfer layer 260 may be formed as a single layer. For example, the HIL 262 may be omitted and the second charge transfer layer 260 may be formed of only the HTL 264. A thickness of the HIL 262 and the HTL 264 may range from about 10 nm to about 200 nm, preferably about 10 nm to about 100 nm, but the present disclosure is not limited thereto.

Similar to the first embodiment, the light-emitting diode 200 according to a second embodiment of the present disclosure may include at least one exciton blocking layer adjacent to the EML 250. For example, the light-emitting diode 200 may further include an electron blocking layer between the EML 250 and the HTL 264 and capable of controlling and preventing transfer of electrons, and/or a hole blocking layer between the ETL 244 and the EML 250 and capable of controlling and preventing transfer of holes.

In the light-emitting diode 200 according to a second embodiment of the present disclosure, the HTL 264 of the second charge transfer layer 260 located between the second electrode 220 and the EML 250 includes the organic compound of Formula 1 or 2. Accordingly, as schematically illustrated in FIG. 5, a difference ($\Delta G'_H$) in HOMO energy level between an HTL and an EML is significantly reduced, and thus an energy barrier between the HTL and the EML may be removed.

That is, by applying the organic compound of Formula 1 or 2 to the HTL, the difference ($\Delta G'_H$) in HOMO energy level between an HTL and an EML becomes identical to or has no significant difference from a difference ($\Delta G_L$) in LUMO energy level between an ETL and an EML. Since balanced numbers of holes and electrons are injected into the EML to thereby form excitons, the number of electrons that do not form excitons and disappear is reduced or these electrons disappear. In addition, light emission efficiently occurs in a luminescent material injected into the EML, not at an interface between the EML and the HTL or the ETL adjacent thereto. Accordingly, the light-emitting diode 200 may exhibit maximized luminous efficiency and operate at a low voltage, and accordingly, power consumption may be reduced.

Figure 6:
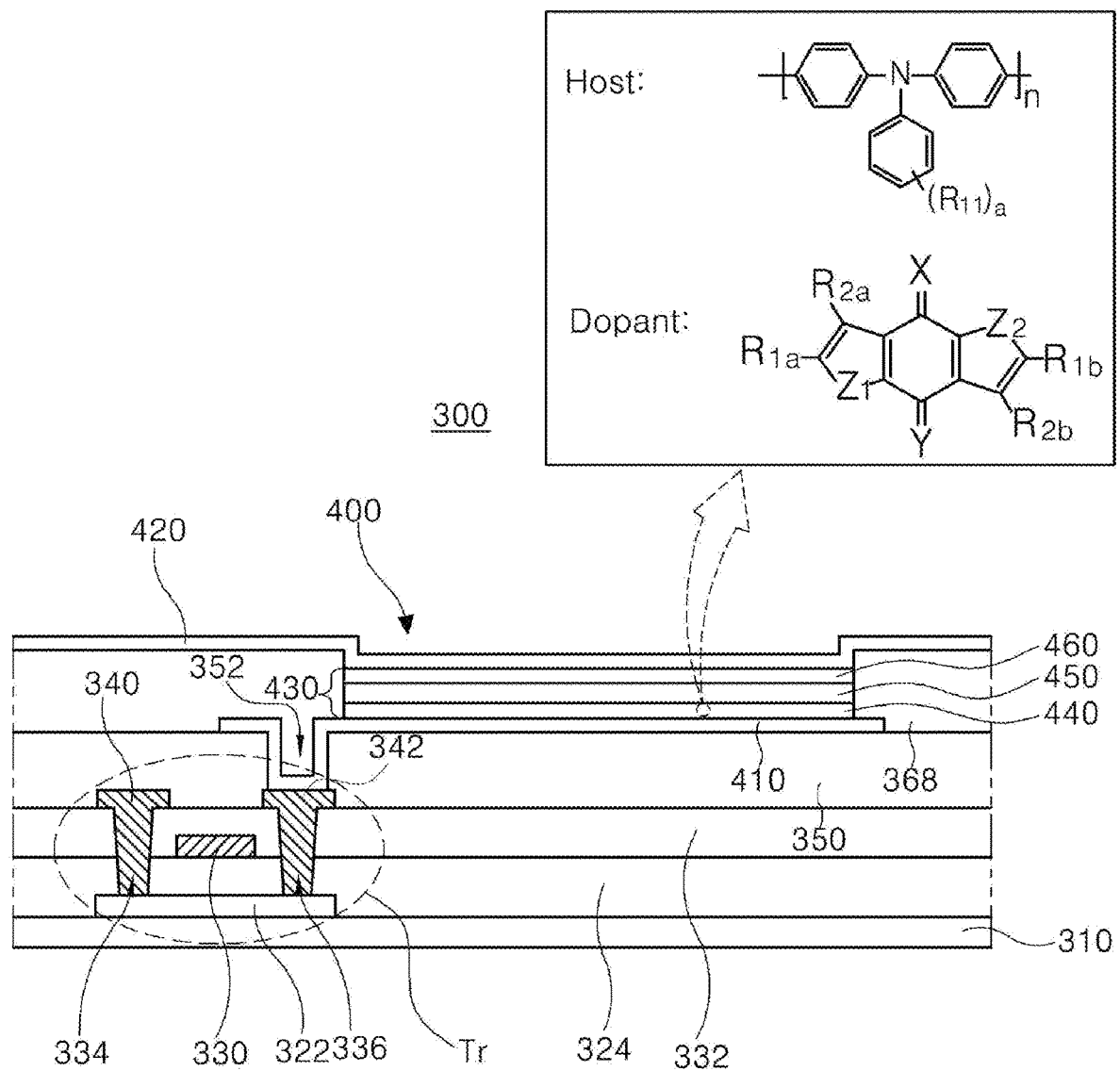
FIG. 6 is a schematic cross-sectional view illustrating a light-emitting display device, which is an example of a light-emitting device employing a light-emitting diode according to an example embodiment of the present disclosure.

Thus, a light-emitting diode, in which the organic compound of Formula 1 or 2 is applied to a hole transfer layer, may be applied to a lighting device or a light-emitting device such as a display device. For example, a light-emitting device including a light-emitting diode in which the organic compound according to the present disclosure is applied to a hole transfer layer will be described. FIG. 6 is a schematic cross-sectional view illustrating a light-emitting display device 300 according to an example embodiment of the present disclosure.

As illustrated in FIG. 6, the light-emitting display device 300 includes a substrate 310, and, on the substrate 310, a driving thin film transistor Tr, which is a driving element, and a light-emitting diode 400 connected to the driving thin film transistor Tr.

A semiconductor layer 322 formed of an oxide semiconductor material or polycrystalline silicon is provided on the substrate 310. When the semiconductor layer 322 is formed of an oxide semiconductor material, a light-shielding pattern (not shown) may not be formed on a lower portion of the semiconductor layer 322, and the light-shielding pattern prevents light from being incident on the semiconductor layer 322, thus preventing the semiconductor layer 322 from being deteriorated by light. Unlike this, the semiconductor layer 322 may be formed of polycrystalline silicon, and in this case, opposite edges of the semiconductor layer 322 may be doped with impurities.

A gate insulating film 324 formed of an insulating material is disposed on the semiconductor layer 322. The gate insulating film 324 may be formed of an inorganic insulating material such as a silicon oxide (SiO2) or a silicon nitride (SiNx). A gate electrode 330 made of a conductive material such as a metal is disposed on the gate insulating film 324 to correspond to a center of the semiconductor layer 322.

An interlayer insulating film 332 formed of an insulating material is disposed on the gate electrode 330. The interlayer insulating film 332 may be formed of an inorganic insulating material such as SiO2 or SiNx, or an organic insulating material such as benzocyclobutene or photo-acryl.

The interlayer insulating film 332 has first and second semiconductor layer contact holes 334 and 336 that expose opposite sides of the semiconductor layer 322. The first and second semiconductor layer contact holes 334 and 336 are located on opposite sides of the gate electrode 330 to be spaced apart from the gate electrode 330. A source electrode 340 and a drain electrode 342, which are formed of a conductive material such as a metal, are disposed on the interlayer insulating film 332.

The source electrode 340 and the drain electrode 342 are spaced apart from each other with respect to the gate electrode 330, and contact opposite sides of the semiconductor layer 322 through the first and second semiconductor contact holes 334 and 336, respectively. The semiconductor layer 322, the gate electrode 330, the source electrode 340, and the drain electrode 342 constitute the driving thin film transistor Tr, which is a driving element.

In FIG. 6, the driving thin film transistor Tr has a coplanar structure in which the gate electrode 330, the source electrode 340, and the drain electrode 342 are disposed on the semiconductor layer 322. Unlike this, the driving thin film transistor Tr may have an inverted staggered structure in which a gate electrode is disposed on a lower portion of a semiconductor layer and a source electrode and a drain electrode are disposed on an upper portion of the semiconductor layer. In this case, the semiconductor layer may be formed of amorphous silicon.

Although not shown, a gate line and a data line cross each other to define a pixel region, and a switching element connected to the gate line and the data line is further formed in the pixel region. The switching element is connected to the driving thin film transistor Tr, which is a driving element. In addition, a power line is parallelly spaced apart from the gate line or the data line, and the driving thin film transistor Tr may further include a storage capacitor configured to constantly maintain a voltage of a gate electrode of the driving thin film transistor Tr, which is a driving element, for one frame.

Meanwhile, a passivation layer 350 having a drain contact hole 352, through which the drain electrode 342 of the driving thin film transistor Tr is exposed, is formed to cover the driving thin film transistor Tr. For example, the passivation layer 350 may be formed of an inorganic insulating material such as SiO2 or SiNx, or an organic insulating material such as photo-acryl.

A first electrode 410 connected to the drain electrode 342 of the driving thin film transistor Tr through the drain contact hole 352 is disposed on the passivation layer 350 in each pixel region. The first electrode 410 may be an anode or a cathode, and may be made of a conductive material having a relatively high work function. For example, the first electrode 410 may be made of a doped or undoped metal oxide such as ITO, IZO, ITZO, ICO, $SnO_2$, $In_2O_3$, Cd:ZnO, $F:SnO_2$, $In:SnO_2$, $Ga:SnO_2$ or AZO, or a metal material including Ni, Pt, Au, Ag, Ir, or carbon nanotubes, other than the above-described metal oxides.

Meanwhile, in a case in which the light-emitting display device 300 of the present disclosure is a top-emission type, a reflective electrode or a reflective layer may be further disposed on a lower portion of the first electrode 410. For example, the reflective electrode or the reflective layer may be formed of an aluminum-palladium-copper (APC) alloy.

In addition, a bank layer 368 is disposed on the passivation layer 350 to cover an edge of the first electrode 410. The bank layer 368 exposes a center of the first electrode 410 to correspond to a pixel region.

An emissive layer 430 is disposed on the first electrode 410. The emissive layer 430 may be formed only as an EML, but may have multiple charge transfer layers to enhance luminous efficiency. For example, FIG. 6 illustrates the emissive layer 430 as including a first charge transfer layer 440, an emitting material layer 450, and a second charge transfer layer 460 that are sequentially stacked between the first electrode 410 and a second electrode 420.

For example, the first charge transfer layer 440 may be a hole transfer layer, and may consist of the HIL 142 (see FIG. 2) and the HTL 144 (see FIG. 2) that are formed of an organic material. The hole transport layer constituting the first charge transfer layer 440 includes the organic compound of Formula 1 or 2. The organic compound may be used as a dopant of the hole transport layer, and in this case, one of the organic materials having a triphenylamine moiety of Formulae 3 to 5 may be used as a host of the hole transport layer.

The emitting material layer 440 may be formed of an inorganic luminescent material or an organic luminescent material. Meanwhile, the second charge transfer layer 450 may be an electron transfer layer, and may consist of the EIL 162 (see FIG. 2) and the ETL 164 (see FIG. 2). For example, the second charge transfer layer 450 may be formed of an inorganic material or an organic material.

The second electrode 420 is disposed above the substrate 310 above which the emissive layer 430 is disposed. The second electrode 420 may be disposed on the entire surface of a display region, may be made of a conductive material having a relatively low work function, and may be a cathode or an anode. For example, the second electrode 420 may be made of Ca, Ba, Ca/Al, LiF/Ca, LiF/Al, $BaF_2$/Al, CsF/Al, $CaCO_3$/Al, $BaF_2$/Ca/Al, Al, Mg, Au:Mg, or Ag:Mg.

FIG. 6 illustrates the light-emitting diode 400 having a normal structure in which the first charge transfer layer 440 as a hole transfer layer is disposed between the first electrode 410 and the emitting material layer 450, and the second charge transfer layer 460 as an electron transfer layer is disposed between the second electrode 420 and the emitting material layer 450.

In another embodiment, a light-emitting diode having an inverted structure in which a first charge transfer layer as an electron transfer layer is disposed between the first electrode 410 and the emitting material layer 450, and a second charge transfer layer as a hole transfer layer is disposed between the second electrode 420 and the emitting material layer 450 may be manufactured. In this case, the organic compound of Formula 1 or 2 may be used in a hole transport layer constituting the second charge transfer layer 460 disposed between the second electrode 420 and the emitting material layer 450.

By applying the organic compound of Formula 1 or 2 to the first charge transfer layer 440 or the second charge transfer layer 460 that may be an HTL, a difference in HOMO energy level between the HTL and the EML 450 may be reduced, and accordingly, a HOMO energy barrier between the HTL and the EML 450 may be removed. By applying the organic compound of Formula 1 or 2 to the first charge transfer layer 440 or the second charge transfer layer 460 that may be an HTL, hole mobility properties may be enhanced. Accordingly, balanced numbers of holes and electrons are injected into the EML 450, and thus the light-emitting diode 400 and the light-emitting display device 300 may exhibit enhanced luminous efficiency and operate at a low voltage, and accordingly, power consumption may be reduced.

Hereinafter, the present disclosure will be described with reference to the following examples, but the present disclosure is not intended to be limited by the technical spirit described in the examples set forth herein.

Synthesis Example 1: Synthesis of Compound SH01

(1) Synthesis of Compound S-1

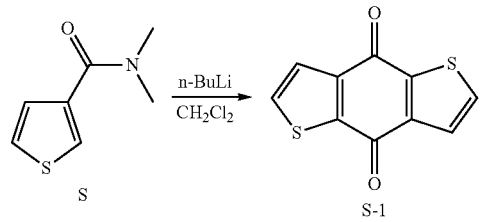

9.0 g (58 mmol) of Compound S was dissolved in 500 ml of anhydrous ether, 49 ml of a 2.5 M butyl lithium (n-BuLi) solution was added dropwise thereto at room temperature, and then the resulting solution was stirred at room temperature for 12 hours. The reaction mixture was poured into ice water and extracted with ethyl acetate to obtain an organic layer, and the organic layer was dried by treatment of anhydrous magnesium sulfate. The obtained reaction product was recrystallized with acetone to obtain 8.56 g of Compound S-1 (yield: 62%).

(2) Synthesis of Compound S-2

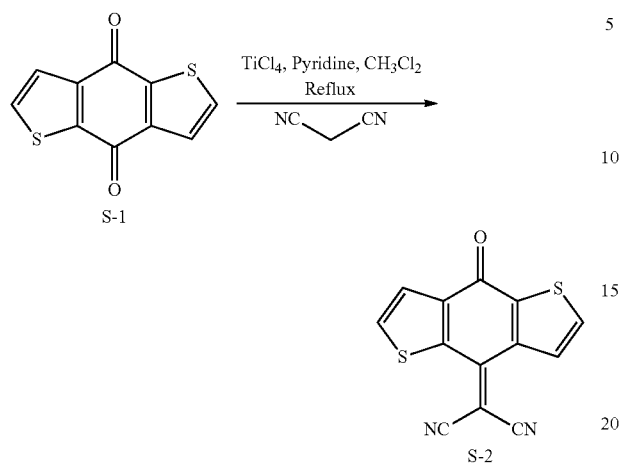

5 g (23 mmol) of Compound S-1, 3.10 g (46 mmol) of malononitrile, 10 ml of pyridine, and 200 ml of chloroform were stirred at room temperature, and 5 ml of TiCl$_4$ was slowly added thereto, and then the reaction mixture was heated while being stirred for 5 hours. After raising the temperature of the reaction mixture to room temperature, the reaction mixture was extracted with CH$_2$Cl$_2$ and H$_2$O, and then the CH$_2$Cl$_2$ solvent, which is an organic layer, was dried by treatment of anhydrous Na$_2$SO$_4$. The obtained reaction product was recrystallized with CH$_2$Cl$_2$ and acetonitrile to obtain 2.74 g of Compound S-2 (yield: 45%).

(3) Synthesis of Compound F-1

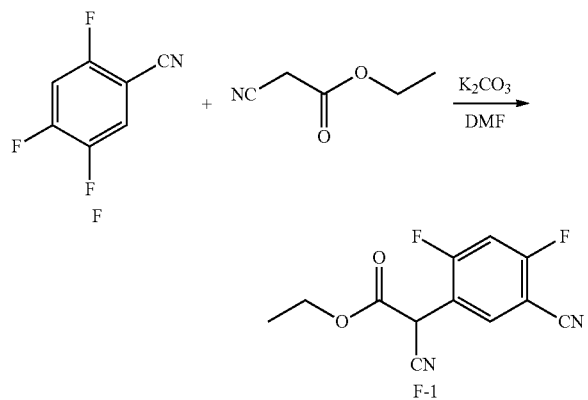

10 g (64 mmol) of Compound F and 14.4 g (128 mmol) of potassium carbonate were placed in a 250 ml 2-neck flask and dissolved in 100 ml of DMF. Then, 9.7 ml (70.4 mmol) of ethyl cyanoacetate was added thereto and the resulting solution was stirred at 80° C. for 16 hours. After the reaction was completed, water and a trace amount of acetic acid were added to the reaction product, followed by stirring for 30 minutes, and then the resulting reaction product was extracted several times using a large amount of chloroform and water and washed with brine, and then the solvent was distilled off under reduced pressure, followed by column chromatography using dichloromethane and hexane as developing solvents, thereby obtaining 14.3 g of Compound F-1 (yield: 90%).

(4) Synthesis of Compound F-2

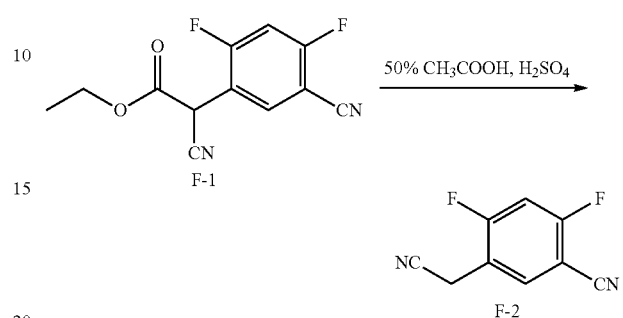

10.0 g (40 mmol) of Compound F-1 was dissolved in a 250 ml 2-neck flask with a mixed solvent of 10 ml of acetic acid and 10 ml of water. 1 ml of sulfuric acid was then added to the resulting solution and heated while being refluxed for 14 hours. After the reaction was completed, the reaction product was cooled to room temperature, ice water was added thereto, followed by extraction using water and ethyl acetate, the obtained ethyl acetate layer was washed again with an aqueous NaHCO$_3$ solution and washed again with water, the product obtained by distilling off the solvent under reduced pressure was subjected to column chromatography using dichloromethane and hexane to obtain 6.05 g of Compound F-2 (yield: 85%).

(5) Synthesis of Compound SH01

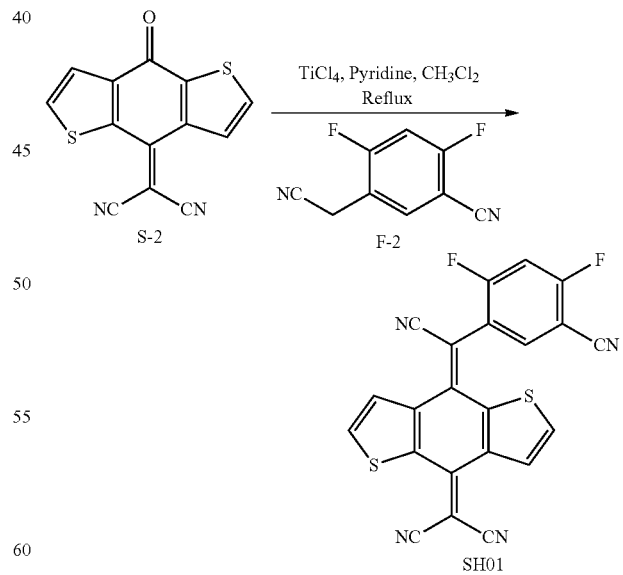

2 g (7.5 mmol) of Compound S-2, 2.66 g (15 mmol) of Compound F-2, 10 ml of pyridine, and 200 ml of chloroform were added and stirred at room temperature, and 5 ml of TiCl$_4$ was slowly added thereto, and then the reaction mixture was heated while being stirred for 5 hours. After raising the temperature of the reaction mixture to room temperature, the reaction mixture was extracted with $CH_2Cl_2$ and $H_2O$, and then the $CH_2Cl_2$ solvent, which is an organic layer, was dried by treatment of anhydrous $Na_2SO_4$. The obtained reaction product was recrystallized with $CH_2Cl_2$ and acetonitrile to obtain 4.34 g of Compound SH01 (yield: 68%).

Synthesis Example 2: Synthesis of Compound SH02

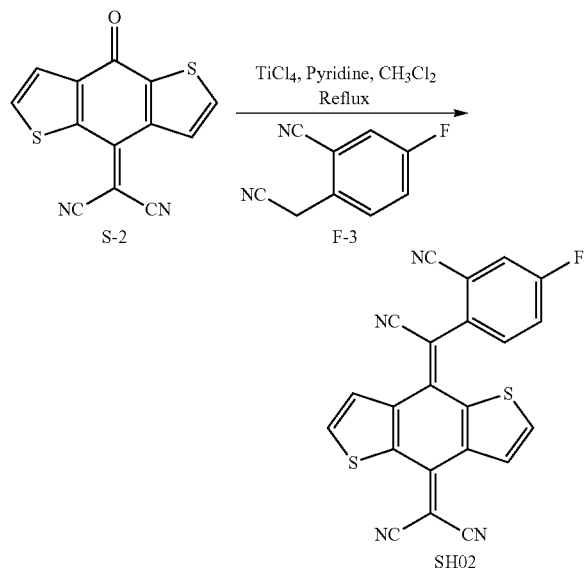

2 g (7.45 mmol) of Compound S-2, 2.39 g (15 mmol) of Compound F-3, 10 ml of pyridine, and 200 ml of chloroform were added and stirred at room temperature, and 5 ml of $TiCl_4$ was slowly added thereto, and then the reaction mixture was heated while being stirred for 5 hours. After raising the temperature of the reaction mixture to room temperature, the reaction mixture was extracted with $CH_2Cl_2$ and $H_2O$, and then the $CH_2Cl_2$ solvent, which is an organic layer, was dried by treatment of anhydrous $Na_2SO_4$. The obtained reaction product was recrystallized with $CH_2Cl_2$ and acetonitrile to obtain 2.17 g of Compound SH02 (yield: 71%).

Synthesis Example 3: Synthesis of Compound SH03

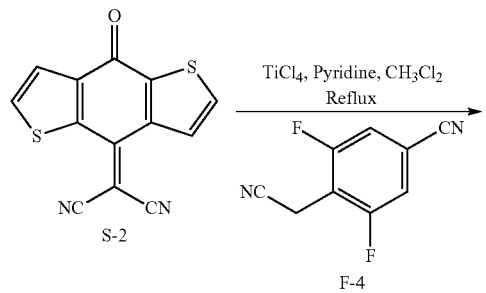

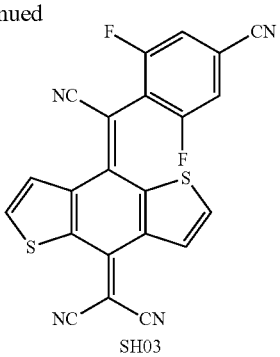

2 g (7.45 mmol) of Compound S-2, 2.66 g (15 mmol) of Compound F-4, 10 ml of pyridine, and 200 ml of chloroform were added and stirred at room temperature, and 5 ml of $TiCl_4$ was slowly added thereto, and then the reaction mixture was heated while being stirred for 5 hours. After raising the temperature of the reaction mixture to room temperature, the reaction mixture was extracted with $CH_2Cl_2$ and $H_2O$, and then the $CH_2Cl_2$ solvent, which is an organic layer, was dried by treatment of anhydrous $Na_2SO_4$. The obtained reaction product was recrystallized with $CH_2Cl_2$ and acetonitrile to obtain 2.52 g of Compound SH03 (yield: 71%).

Synthesis Example 4: Synthesis of Compound SH04

(1) Synthesis of Compound S-4

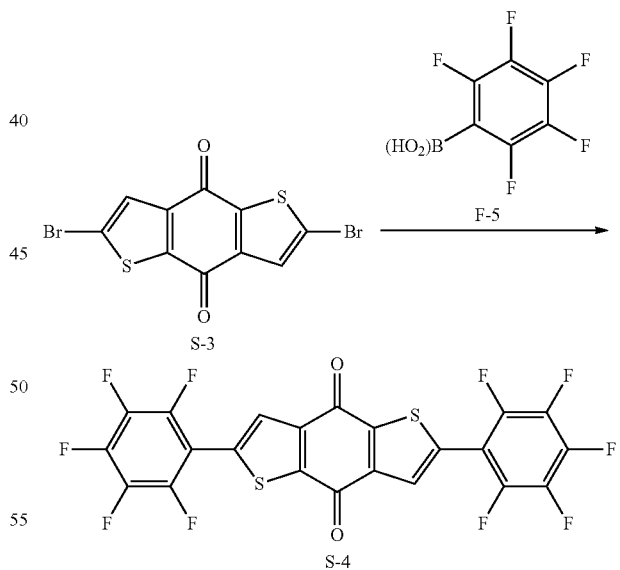

3.0 g (8 mmol) of Compound S-3, 3.56 g (17.0 mmol) of perfluorophenylboronic acid, 0.22 g (0.41 mmol) of tetrakis (triphenylphosphine)palladium(0), and 5.0 g (36.18 mmol) of potassium carbonate were added to a mixed solution of 90 ml of 1,4-dioxane and 30 ml of water, and the resulting solution was stirred at 80° C. for 4 hours. After the reaction was completed, the reaction product was extracted using water and ethyl acetate, concentrated, and then subjected to column separation using dichloromethane and n-hexane.

Subsequently, the product was precipitated using dichloromethane and petroleum ether, and then the precipitate was filtered, thereby obtaining 3.42 g of Compound S-4 (yield: 78%).

(2) Synthesis of Compound S-5

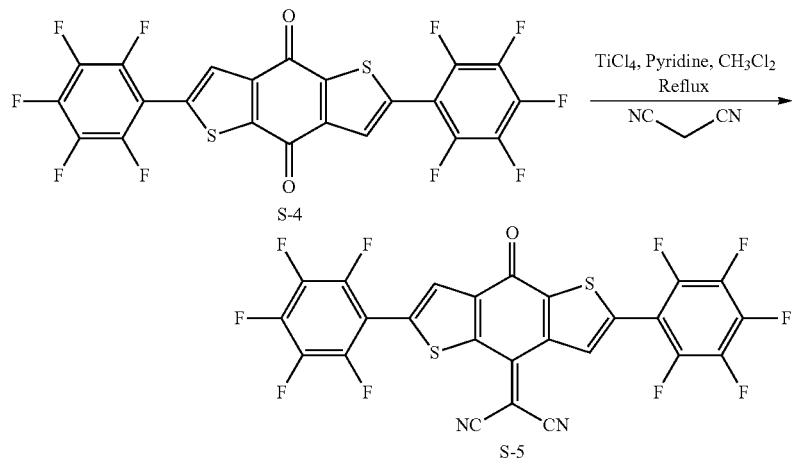

3 g (5.4 mmol) of Compound S-4, 0.74 g (11 mmol) of malononitrile, 7 ml of pyridine, and 200 ml of chloroform were added and stirred at room temperature, and 4 ml of $TiCl_4$ was slowly added thereto, and then the reaction mixture was heated while being stirred for 5 hours. After raising the temperature of the reaction mixture to room temperature, the reaction mixture was extracted with $CH_2Cl_2$ and $H_2O$, and then the $CH_2Cl_2$ solvent, which is an organic layer, was dried by treatment of anhydrous $Na_2SO_4$. The obtained reaction product was recrystallized with $CH_2Cl_2$ and acetonitrile to obtain 1.34 g of Compound S-5 (yield: 41%).

(3) Synthesis of Compound SH04

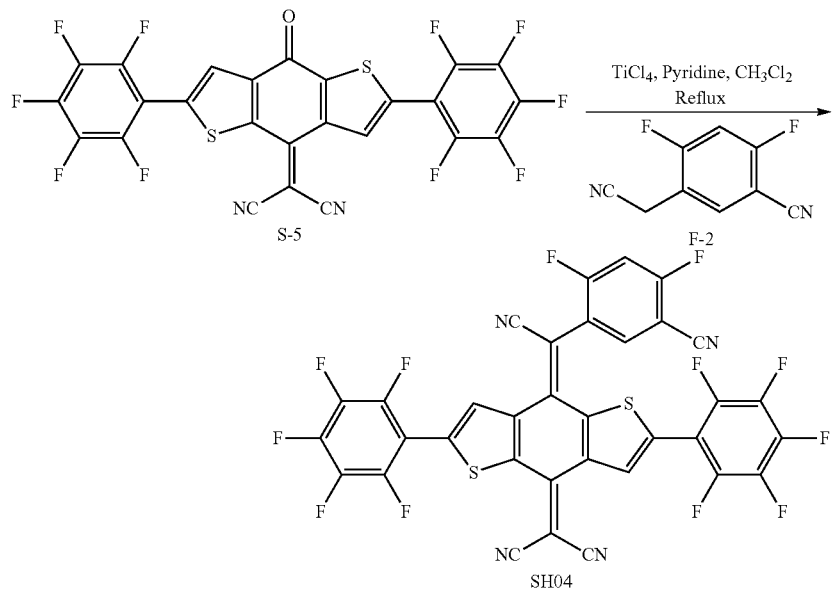

1 g (1.67 mmol) of Compound S-5, 0.59 g (3.3 mmol) of Compound F-2, 5 ml of pyridine, and 100 ml of chloroform were added and stirred at room temperature, and 2.5 ml of TiCl$_4$ was slowly added thereto, and then the reaction mixture was heated while being stirred for 5 hours. After raising the temperature of the reaction mixture to room temperature, the reaction mixture was extracted with CH$_2$Cl$_2$ and H$_2$O, and then the CH$_2$Cl$_2$ solvent, which is an organic layer, was dried by treatment of anhydrous Na$_2$SO$_4$. The obtained reaction product was recrystallized with CH$_2$Cl$_2$ and acetonitrile to obtain 0.48 g of Compound SH04 (yield: 38%).

Comparative Synthesis Example 1: Synthesis of Compound TH01

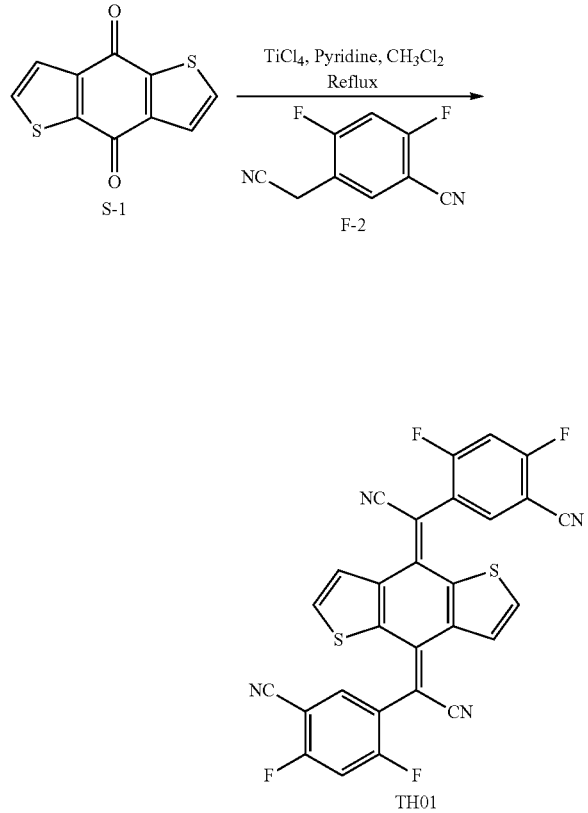

2 g (7.5 mmol) of Compound S-1, 2.66 g (15 mmol) of Compound F-2, 15 ml of pyridine, and 200 ml of chloroform were added and stirred at room temperature, and 6 ml of TiCl$_4$ was slowly added thereto, and then the reaction mixture was heated while being stirred for 5 hours. After raising the temperature of the reaction mixture to room temperature, the reaction mixture was extracted with CH$_2$Cl$_2$ and H$_2$O, and then the CH$_2$Cl$_2$ solvent, which is an organic layer, was dried by treatment of anhydrous Na$_2$SO$_4$. The obtained reaction product was recrystallized with CH$_2$Cl$_2$ and acetonitrile to obtain 4.22 g of Compound TH01 (yield: 86%).

Comparative Synthesis Example 2: Synthesis of Compound TH02

2 g (9.1 mmol) of Compound S-1, 2.91 g (18 mmol) of Compound F-3, 15 ml of pyridine, and 200 ml of chloroform were added and stirred at room temperature, and 6 ml of TiCl$_4$ was slowly added thereto, and then the reaction mixture was heated while being stirred for 5 hours. After raising the temperature of the reaction mixture to room temperature, the reaction mixture was extracted with CH$_2$Cl$_2$ and H$_2$O, and then the CH$_2$Cl$_2$ solvent, which is an organic layer, was dried by treatment of anhydrous Na$_2$SO$_4$. The obtained reaction product was recrystallized with CH$_2$Cl$_2$ and acetonitrile to obtain 3.76 g of Compound TH02 (yield: 85%).

Comparative Synthesis Example 3: Synthesis of Compound TH03

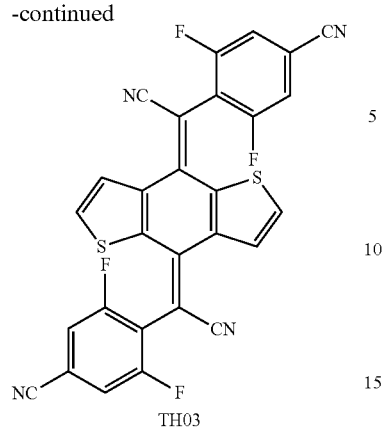

TH03

2 g (9.1 mmol) of Compound S-1, 3.23 g (18 mmol) of Compound F-4, 15 ml of pyridine, and 200 ml of chloroform were added and stirred at room temperature, and 6 ml of $TiCl_4$ was slowly added thereto, and then the reaction mixture was heated while being stirred for 5 hours. After raising the temperature of the reaction mixture to room temperature, the reaction mixture was extracted with $CH_2Cl_2$ and $H_2O$, and then the $CH_2Cl_2$ solvent, which is an organic layer, was dried by treatment of anhydrous $Na_2SO_4$. The obtained reaction product was recrystallized with $CH_2Cl_2$ and acetonitrile to obtain 4.02 g of Compound TH03 (yield: 82%).

Comparative Synthesis Example 4: Synthesis of Compound TH04

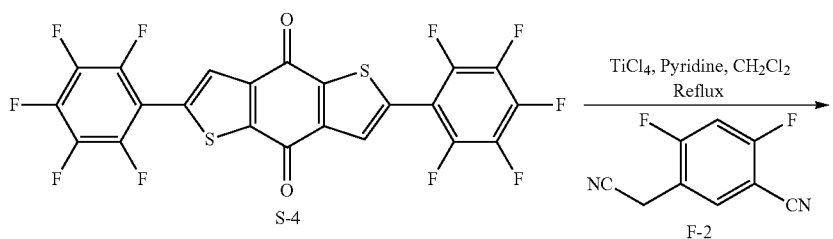

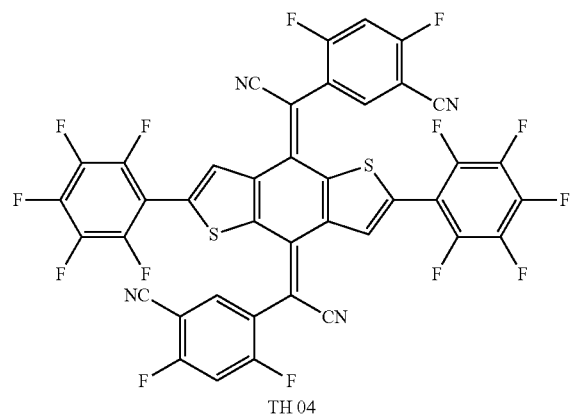

TH 04

1 g (1.81 mmol) of Compound S-4, 0.65 g (3.62 mmol) of Compound F-2, 5 ml of pyridine, and 100 ml of chloroform were added and stirred at room temperature, and 3 ml of TiCl$_4$ was slowly added thereto, and then the reaction mixture was heated while being stirred for 5 hours. After raising the temperature of the reaction mixture to room temperature, the reaction mixture was extracted with CH$_2$Cl$_2$ and H$_2$O, and then the CH$_2$Cl$_2$ solvent, which is an organic layer, was dried by treatment of anhydrous Na$_2$SO$_4$. The obtained reaction product was recrystallized with CH$_2$Cl$_2$ and acetonitrile to obtain 1.16 g of Compound TH04 (yield: 74%).

Example 1: Manufacture of Light-Emitting Diode

A light-emitting diode was manufactured using Compound SH01 synthesized according to Synthesis Example 1 as a dopant of a hole transport layer (HTL). ITO glass was patterned such that the ITO glass had a light-emitting area of 3 mm×3 mm, and then washed. Subsequently, an emissive layer and a cathode were stacked according to the following order. A hole injection layer (HIL) (PEDOT:PSS, spin coating (7,000 rpm) and then heating at 150° C. for 30 minutes; 30 nm) and an HTL (TFB:SH01 (weight ratio of 2:1 to 1:2)) were transferred to a vacuum chamber, and then subjected to deposition (1×10$^{-6}$ Torr, 20 nm), an emitting material layer (EML) (InP/ZnSe/ZnS, spin coating (2,000 rpm), and then heating at 80° C. for 1 hour; 20 nm), an electron transport layer (ETL) (2-[4-(9,10-di-2-naphthalenyl-2-anthracenyl)phenyl]-1-phenyl-1H-benzimidazole: LIQ (50%), and a substrate were transferred to the vacuum chamber and subjected to deposition (1×10$^{-6}$ Torr, 40 nm), and then a cathode (Al, deposition (1×10$^{-6}$ Torr), 80 nm) was formed on the resulting structure.

After deposition, for film formation, the resulting structure was moved from the deposition chamber into a dry box, followed by encapsulation using UV-curable epoxy and a moisture getter. The manufactured light-emitting diode has an emission area of 9 mm$^2$.

Example 2: Manufacture of Light-Emitting Diode

A light-emitting diode was manufactured in the same manner as in Example 1, except that Compound SH02 synthesized according to Synthesis Example 2 was used as a dopant of an HTL.

Example 3: Manufacture of Light-Emitting Diode

A light-emitting diode was manufactured in the same manner as in Example 1, except that Compound SH03 synthesized according to Synthesis Example 3 was used as a dopant of an HTL.

Example 4: Manufacture of Light-Emitting Diode

A light-emitting diode was manufactured in the same manner as in Example 1, except that Compound SH04 synthesized according to Synthesis Example 4 was used as a dopant of an HTL.

Comparative Example 1: Manufacture of Light-Emitting Diode

A light-emitting diode was manufactured in the same manner as in Example 1, except that only TFB was used in an HTL without using a dopant.

Comparative Example 2: Manufacture of Light-Emitting Diode

A light-emitting diode was manufactured in the same manner as in Example 1, except that Compound TH01 prepared according to Comparative Synthesis Example 1 was used as a dopant of an HTL.

Comparative Example 3: Manufacture of Light-Emitting Diode

A light-emitting diode was manufactured in the same manner as in Example 1, except that Compound TH02 prepared according to Comparative Synthesis Example 2 was used as a dopant of an HTL.

Comparative Example 4: Manufacture of Light-Emitting Diode

A light-emitting diode was manufactured in the same manner as in Example 1, except that Compound TH03 prepared according to Comparative Synthesis Example 3 was used as a dopant of an HTL.

Comparative Example 5: Manufacture of Light-Emitting Diode

A light-emitting diode was manufactured in the same manner as in Example 1, except that Compound TH04 prepared according to Comparative Synthesis Example 4 was used as a dopant of an HTL.

Experimental Example: Evaluation of Physical Characteristics of Light-Emitting Diodes Each of the light-emitting diodes manufactured according to Examples 1 to 4 and Comparative Examples 1 to 5 was connected to an external power source, and electroluminescent (EL) characteristics of all the diodes manufactured in the present disclosure were evaluated using a constant current source (KEITHLEY) and a photometer PR650 at room temperature. In particular, driving voltage (V), current efficiency (Cd/A), external quantum efficiency (EQE), and color coordinates for a luminescence wavelength of the light-emitting diodes of Examples 1 to 4 and Comparative Examples 1 to 5 were measured. The results thereof are shown in Table 1 below.

TABLE 1

EL characteristics of light-emitting diodes

| | | 10 mA/cm$^2$ | | | | |
| --- | --- | --- | --- | --- | --- | --- |
| Sample | HTL | V | Cd/A | EQE (%) | CIEx | CIEy |
| Example 1 | TFB:SH01 | 5.2 | 4.03 | 5.47 | 0.681 | 0.318 |
| Example 2 | TFB:SH02 | 5.2 | 3.78 | 5.31 | 0.682 | 0.317 |
| Example 3 | TFB:SH03 | 5.1 | 3.79 | 5.43 | 0.681 | 0.317 |
| Example 4 | TFB:SH04 | 5.6 | 3.33 | 4.78 | 0.679 | 0.317 |
| Comparative Example 1 | TFB | 7.2 | 1.68 | 2.15 | 0.662 | 0.321 |
| Comparative Example 2 | TFB:TH01 | 5.6 | 2.18 | 3.20 | 0.678 | 0.316 |
| Comparative Example 3 | TFB:TH02 | 5.9 | 1.68 | 2.81 | 0.683 | 0.312 |
| Comparative Example 4 | TFB:TH03 | 6.0 | 2.23 | 3.30 | 0.679 | 0.318 |
| Comparative Example 5 | TFB:TH04 | 6.1 | 1.89 | 3.03 | 0.682 | 0.313 |

As shown in Table 1, compared to the light-emitting diode including an HTL formed only of TFB, the light-emitting diodes including an HTL formed by doping TFB with the organic compound synthesized according to the present disclosure exhibited a maximum voltage drop of 29.2%, a maximum increase of 139.9% in power efficiency, and a maximum increase of 154.4% in EQE. In addition, compared to the light-emitting diodes each including an HTL formed by doping TFB with the organic compound synthesized according to the corresponding comparative synthesis example, the light-emitting diodes each including an HTL formed by doping TFB with the organic compound synthesized according to the present disclosure exhibited a maximum voltage drop of 16.4%, a maximum increase of 139.9% in power efficiency, and a maximum increase of 94.7% in EQE. From these results, it was confirmed that a light-emitting diode and a light-emitting device suitable for low-voltage operation and having significantly enhanced luminous efficiency and quantum efficiency could be realized by applying the organic compounds synthesized according to the present disclosure to an HTL.

As is apparent from the foregoing description, the present disclosure provides an organic compound having, as a core, a fused heteroaromatic ring having multiple exocyclic double bonds and substituted with functional groups having excellent electron withdrawing properties through each exocyclic double bond, and a light-emitting diode and a light-emitting device each including the organic compound.

Since the organic compound according to the present disclosure has, as a core, a fused heteroaromatic ring having multiple exocyclic double bonds, a HOMO energy bandgap between a hole transfer layer and an emitting material layer can be significantly reduced using the organic compound of the present disclosure in the hole transfer layer. In addition, since the organic compound is substituted with multiple functional groups having excellent electron withdrawing properties through the exocyclic double bonds, hole mobility can be enhanced.

When the organic compound according to the present disclosure is applied to a hole transfer layer, balanced numbers of holes and electrons can be injected into an emitting material layer, and thus effectively form excitons without loss of holes and electrons, thereby contributing to luminescence. Accordingly, a light-emitting diode and a light-emitting device that have enhanced luminous efficiency, and can operate at a low voltage and reduce power consumption can be realized and manufactured.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present invention cover the modifications and variations of the present disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having the following structure of Formula 1:

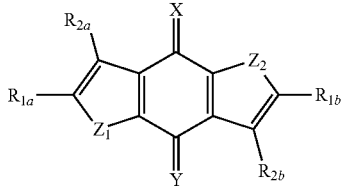

Formula 1 wherein:
$R_{1a}$, $R_{1b}$, $R_{2a}$ and $R_{2b}$ are independently hydrogen, halogen, cyano, nitro, amine, unsubstituted or substituted $C_1$-$C_{20}$ aliphatic ester, unsubstituted or substituted $C_1$-$C_{20}$ alkyl amide, unsubstituted or substituted $C_1$-$C_{20}$ alkyl group, unsubstituted or substituted $C_1$-$C_{20}$ alkoxy group, unsubstituted or substituted $C_1$-$C_{20}$ alkyl amine group, unsubstituted or substituted $C_5$-$C_{30}$ aryl, unsubstituted or substituted $C_4$-$C_{30}$ heteroaryl, unsubstituted or substituted $C_5$-$C_{30}$ aralkyl, unsubstituted or substituted $C_4$-$C_{30}$ heteroaralkyl, unsubstituted or substituted $C_5$-$C_{30}$ aralkoxy, unsubstituted or substituted $C_4$-$C_{30}$ heteroaralkoxy, unsubstituted or substituted $C_5$-$C_{30}$ aryl amine, or unsubstituted or substituted $C_4$-$C_{30}$ heteroaryl amine;

X is oxygen or $CR_5R_6$, wherein $R_5$ and $R_6$ are independently halogen, haloalkyl, cyano, nitro, $C_1$-$C_{20}$ alkyl, $C_5$-$C_{30}$ aryl, or $C_4$-$C_{30}$ heteroaryl, wherein each $C_1$-$C_{20}$ alkyl, $C_5$-$C_{30}$ aryl, and $C_4$-$C_{30}$ heteroaryl is optionally substituted with at least one substituent selected from the group consisting of cyano, nitro, and halogen;

Y is oxygen or $CR_7R_8$, wherein $R_7$ and $R_8$ are independently halogen, haloalkyl, cyano, nitro, $C_1$-$C_{20}$ alkyl, $C_5$-$C_{30}$ aryl, or $C_4$-$C_{30}$ heteroaryl, wherein each $C_1$-$C_{20}$ alkyl, $C_5$-$C_{30}$ aryl, and $C_4$-$C_{30}$ heteroaryl is optionally substituted with at least one substituent selected from the group consisting of cyano, nitro, and halogen, provided that X and Y are not the same; and $Z_1$ and $Z_2$ are each independently $NR_3$, S, or O, wherein $R_3$ is H or an unsubstituted or substituted $C_1$-$C_{20}$ alkyl group.

2. The compound of claim 1, wherein $R_{2a}$ and $R_{2b}$ are both hydrogen.

3. The compound of claim 1, wherein $R_{1a}$ and $R_{1b}$ are both hydrogen.

4. The compound of claim 1, wherein $R_{1a}$ and $R_{1b}$ both have the following structure:

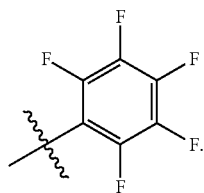 [SMILES: *c1c(F)c(F)c(F)c(F)c1F]

5. The compound of claim 1, wherein X is $CR_5R_6$.

6. The compound of claim 5, wherein $R_5$ and $R_6$ have one of the following structures:

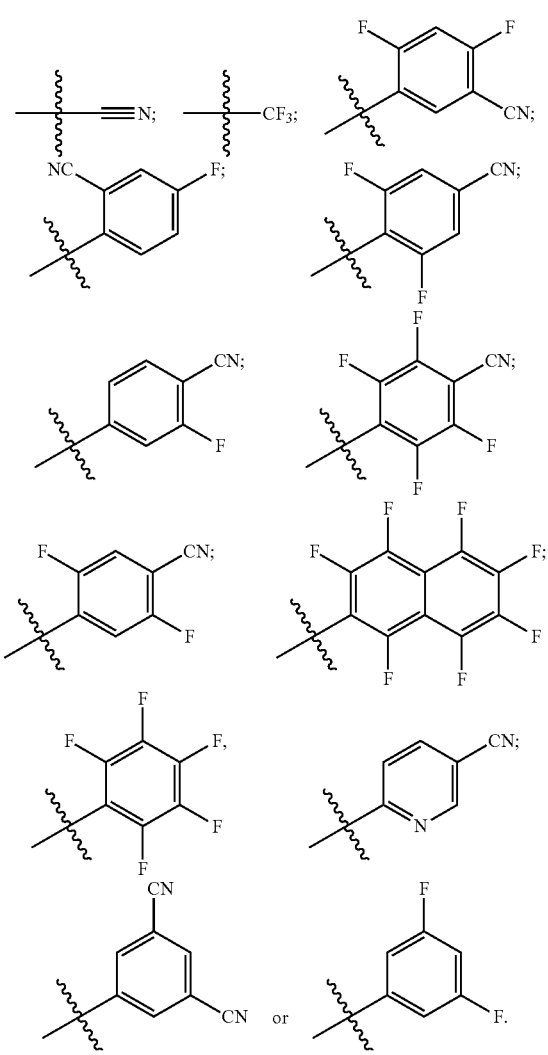

7. The compound of claim 1, wherein Y is $CR_7R_8$.

8. The compound of claim 7, wherein $R_7$ and $R_8$ both have the following chemical structure:

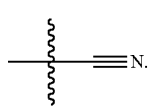 [SMILES: *C#N]

9. The compound of claim 1, wherein $Z_1$ and $Z_2$ are both S.

10. The compound of claim 1, wherein the compound has one of the following structures:

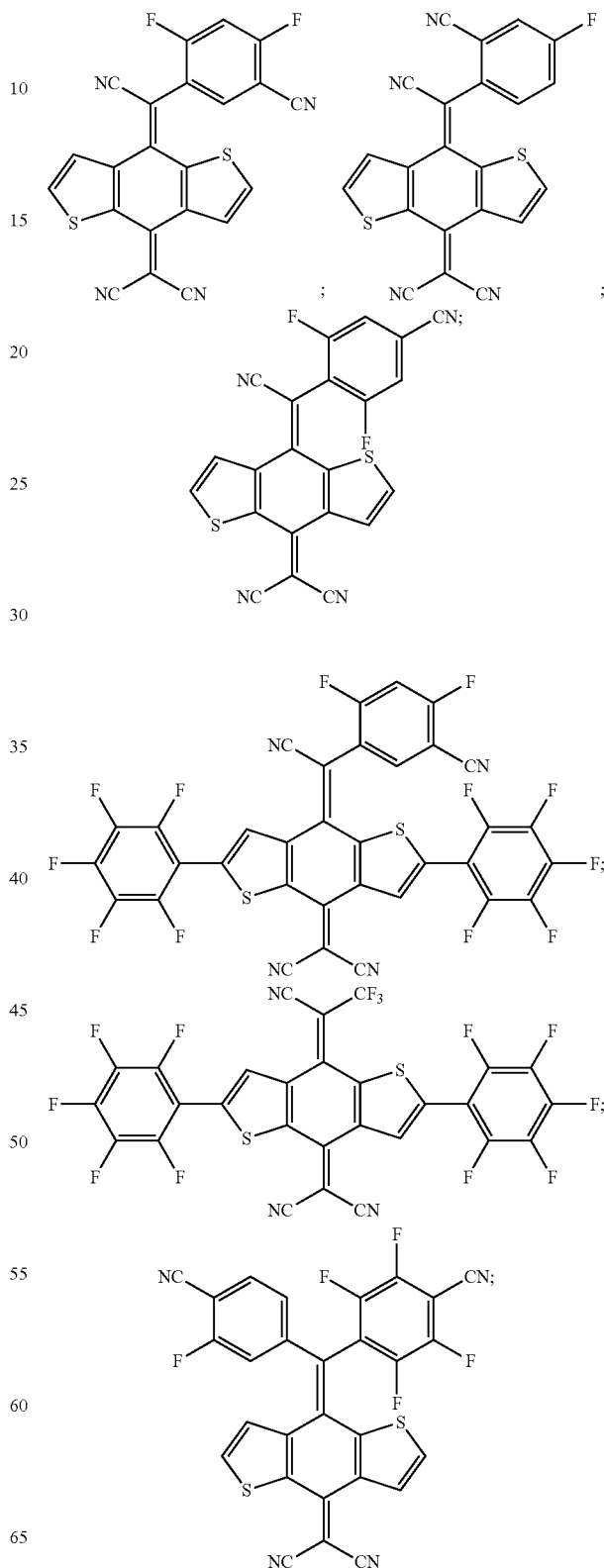

-continued

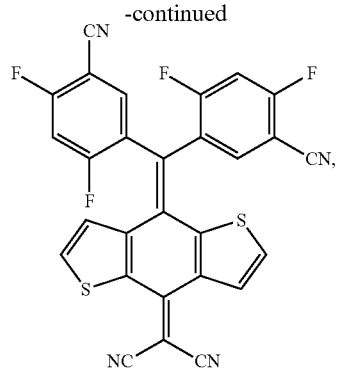

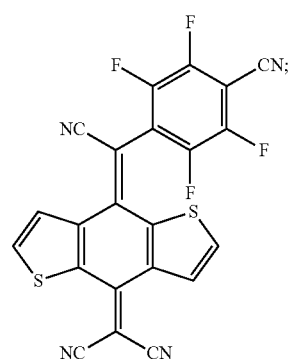

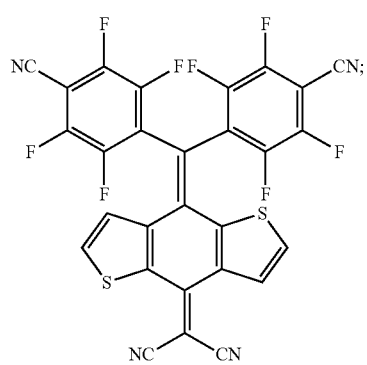

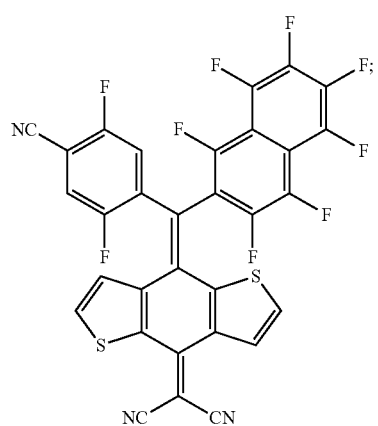

-continued

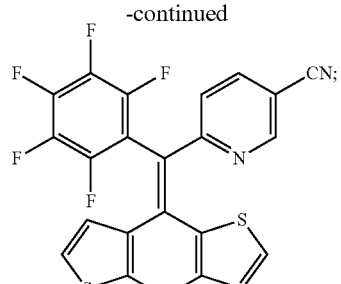

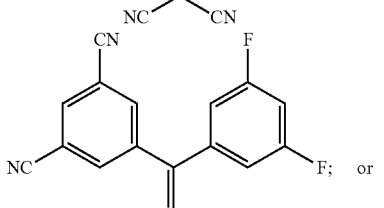

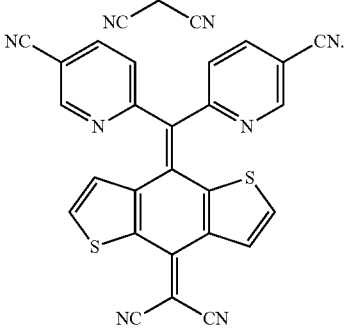 or

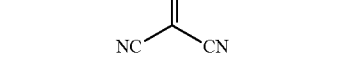

11. A light-emitting diode comprising:
a first electrode and a second electrode facing each other;
an emissive layer interposed between the first and second electrode, wherein the emissive layer comprises a hole transfer layer having the compound according to claim 1.

12. The light-emitting diode of claim 11, wherein the hole transfer layer comprises:
a host material having one of the following structures:

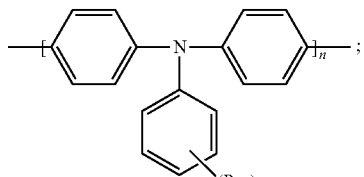

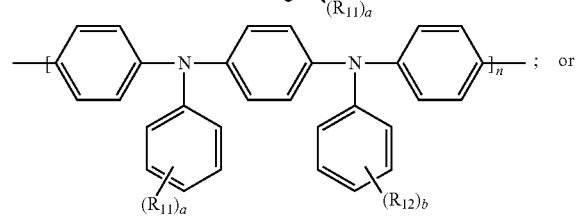

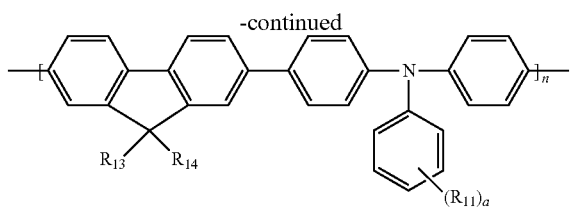

wherein $R_{11}$, $R_{12}$, $R_{13}$ and $R_{14}$ are, at each occurrence, independently unsubstituted or substituted linear or branched $C_1$-$C_{20}$ alkyl, unsubstituted or substituted $C_1$-$C_{20}$ alkoxy, unsubstituted or substituted $C_5$-$C_{30}$ aryl, or unsubstituted or substituted $C_4$-$C_{30}$ heteroaryl;

a and b are, at each occurrence, independently, an integer of 1 to 4; and n is an integer greater than 0.

13. The light emitting diode of claim 12, wherein the compound is doped in an amount of about 1 wt % to about 50 wt %.

14. A light emitting device comprising the light emitting diode of claim 11.

15. The light emitting device of claim 14, wherein the device includes:
  a substrate, wherein the light emitting diode is disposed on an upper portion of the substrate; and
  a driving device disposed between the substrate and the light emitting diode and connected to the light emitting diode.

16. The compound of claim 1, wherein $R_5$ and $R_6$ have one of the following structures:

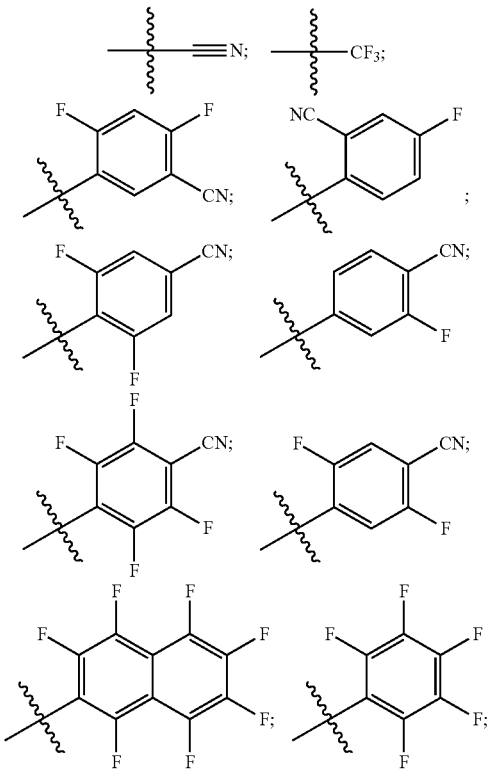

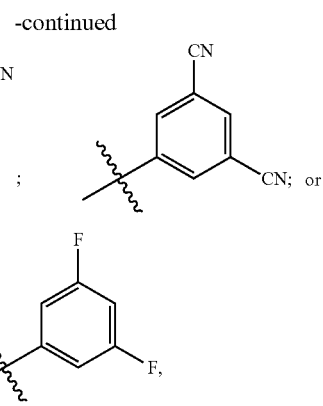

and wherein at least one of $R_5$ and $R_6$ is selected from:

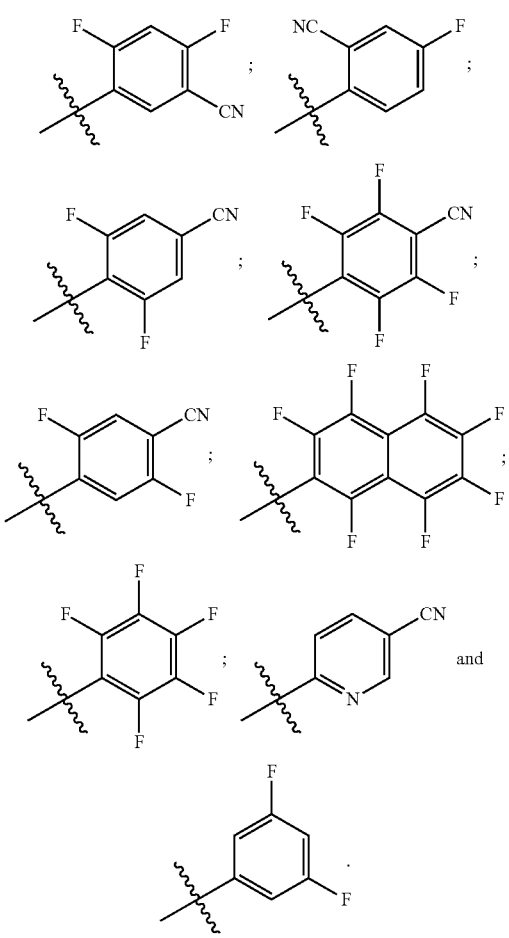

17. The light emitting diode of claim 11, wherein $R_5$ and $R_6$ have one of the following structures:

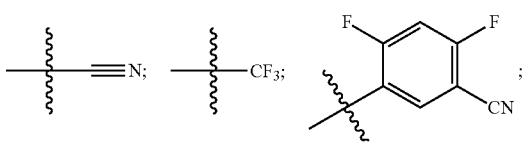

-continued
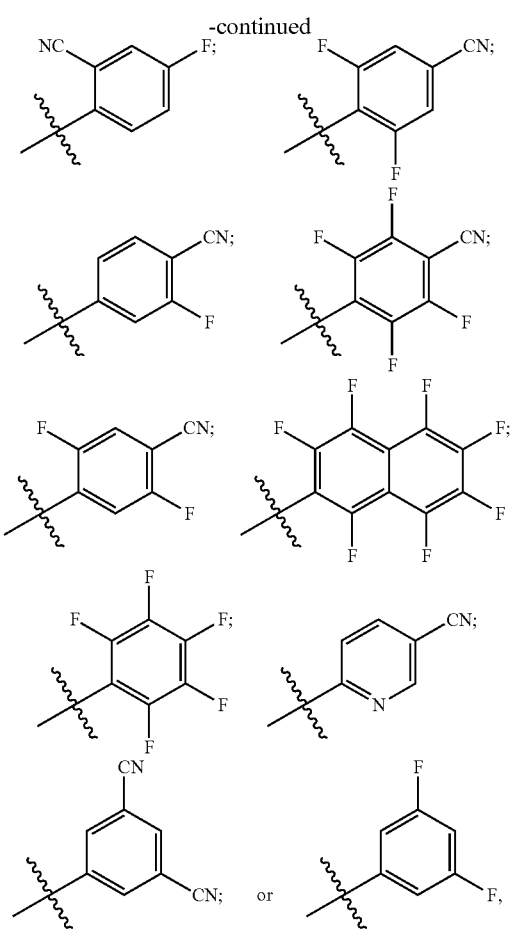
wherein at least one of R₅ and R₆ is selected from:
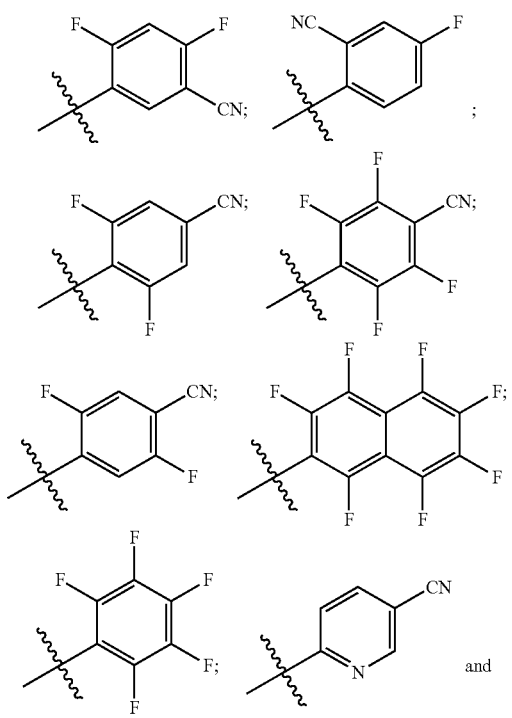
and
-continued
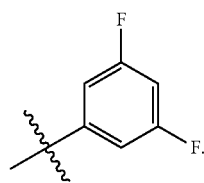
18. The light emitting device of claim 14, wherein R₅ and R₆ have one of the following structures:
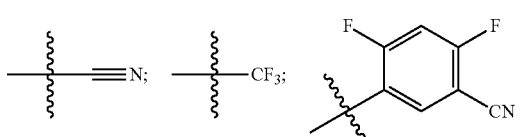
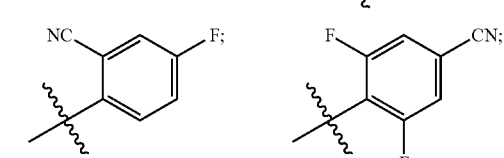
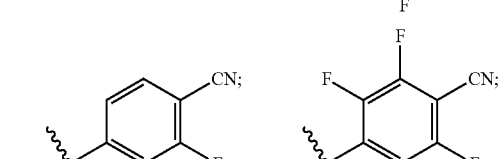
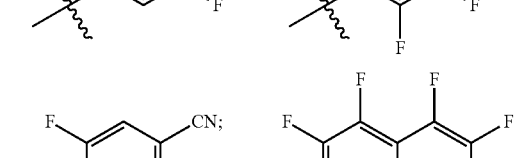
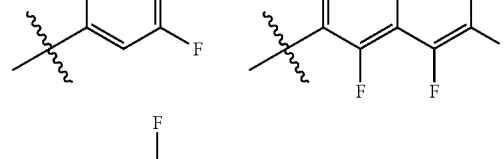
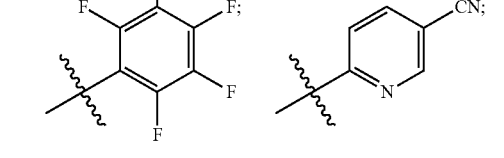
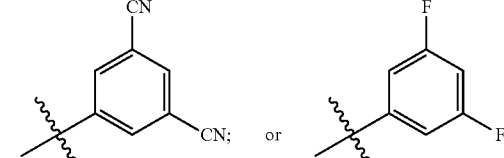
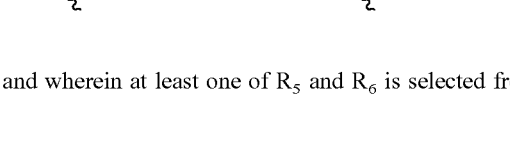
and wherein at least one of R₅ and R₆ is selected from:
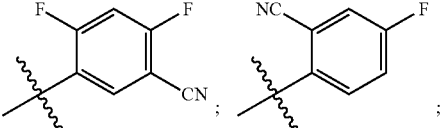

-continued
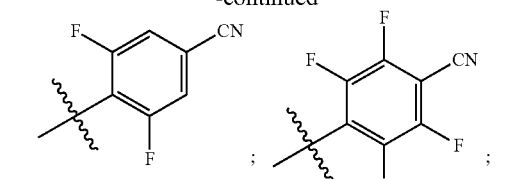
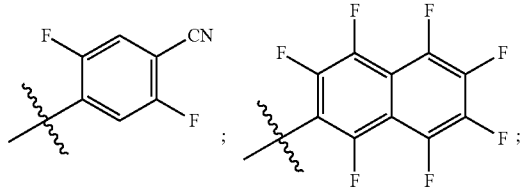
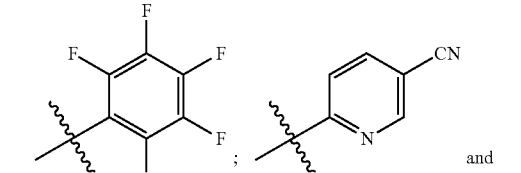
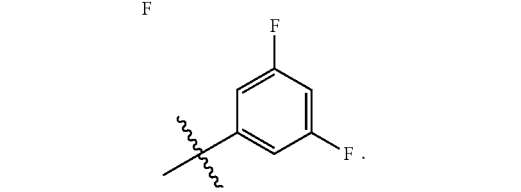
* * * * *